US009797907B2

(12) United States Patent
Goldenberg et al.

(10) Patent No.: US 9,797,907 B2
(45) Date of Patent: Oct. 24, 2017

(54) ISOLATION, DETECTION, DIAGNOSIS AND/OR CHARACTERIZATION OF CIRCULATING TROP-2-POSITIVE CANCER CELLS

(71) Applicant: Immunomedics, Inc., Morris Plains, NJ (US)

(72) Inventors: David M. Goldenberg, Mendham, NJ (US); Hans J. Hansen, Picayune, MS (US); Chien-Hsing Chang, Downingtown, PA (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 15/135,758

(22) Filed: Apr. 22, 2016

(65) Prior Publication Data

US 2016/0313339 A1    Oct. 27, 2016

Related U.S. Application Data

(60) Provisional application No. 62/151,169, filed on Apr. 22, 2015.

(51) Int. Cl.
| | | |
|---|---|---|
| *A61K 47/48* | (2006.01) | |
| *G01N 33/574* | (2006.01) | |
| *G01N 1/40* | (2006.01) | |
| *A61K 31/4745* | (2006.01) | |

(52) U.S. Cl.
CPC ... *G01N 33/57492* (2013.01); *A61K 31/4745* (2013.01); *A61K 47/486* (2013.01); *A61K 47/48384* (2013.01); *A61K 47/48584* (2013.01); *A61K 47/48592* (2013.01); *A61K 47/48615* (2013.01); *G01N 1/405* (2013.01); *G01N 33/574* (2013.01); *G01N 33/57488* (2013.01); *G01N 2001/4038* (2013.01); *G01N 2333/705* (2013.01)

(58) Field of Classification Search
CPC ............................. A61K 47/48; G01N 33/574
USPC ............................................. 424/133.1, 181.1
See application file for complete search history.

(56) References Cited

U.S. PATENT DOCUMENTS

| | | |
|---|---|---|
| 4,036,945 A | 7/1977 | Haber |
| 4,046,722 A | 9/1977 | Rowland |
| 4,200,690 A | 4/1980 | Root et al. |
| 4,331,647 A | 5/1982 | Goldenberg |
| 4,359,457 A | 11/1982 | Neville et al. |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Howthorne |
| 4,916,213 A | 4/1990 | Scannon et al. |
| 4,918,163 A | 4/1990 | Young |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,112,954 A | 5/1992 | Abrams et al. |
| 5,122,368 A | 6/1992 | Greenfield et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,530,101 A | 6/1996 | Queen et al. |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,679,640 A | 10/1997 | Gaeta et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,708,146 A | 1/1998 | Willner et al. |
| 5,716,595 A | 2/1998 | Goldenberg |

(Continued)

FOREIGN PATENT DOCUMENTS

| | | |
|---|---|---|
| DE | 10034607 | 2/2002 |
| EP | 0253202 | 1/1988 |

(Continued)

OTHER PUBLICATIONS

US 6,558,648, 05/2003, Griffiths et al. (withdrawn)
Fong et al. (British Journal of Cancer, 2008, 99: 1290-1295).*
Clinical Trial NCT01631552 (version of Jun. 28, 2012).*
Alberti et al., "Biochemical characterization of Trop-2, a cell surface molecule expressed by human carcinomas: formal proof that the monoclonal antibodies T16 and MOv-16 recognize Trop-2", Hybridoma. Oct. 1992;11(5):539-45.

(Continued)

*Primary Examiner* — Yan Xiao
(74) *Attorney, Agent, or Firm* — Richard A. Nakashima

(57) ABSTRACT

Described herein are compositions and methods of use of anti-Trop-2 antibodies or antigen-binding fragment thereof to isolate, enrich, detect, diagnose and/or characterize circulating tumor cells (CTCs) from patients with a Trop-2 positive cancer. Preferably, the antibody is an RS7, 162-46.2 or MAB650 antibody. The compositions and methods are of use to detect, diagnose and/or treat metastatic Trop-2$^+$ cancers, such as breast, ovarian, cervical, endometrial, lung, prostate, colon, rectum, stomach, esophageal, bladder, renal, pancreatic, thyroid, epithelial or head-and-neck cancer.

15 Claims, 4 Drawing Sheets

(56) References Cited

U.S. PATENT DOCUMENTS

Figure 1:
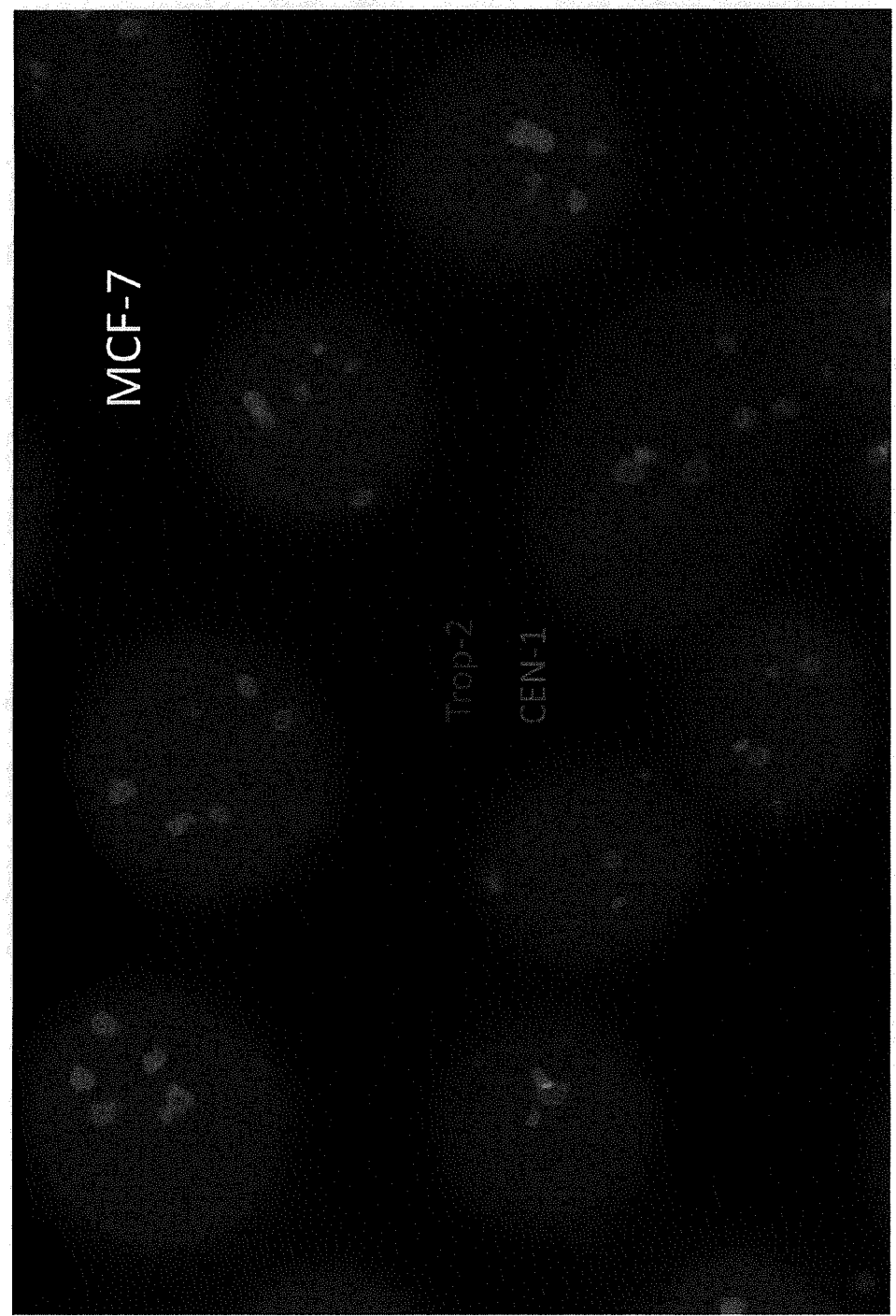

| | | |
|---|---|---|
| 5,736,119 A | 4/1998 | Goldenberg et al. |
| 5,750,105 A | 5/1998 | Newman et al. |
| 5,776,456 A | 7/1998 | Anderson et al. |
| 5,789,554 A | 8/1998 | Leung et al. |
| 5,792,845 A | 8/1998 | O'Reilly et al. |
| 5,795,967 A | 8/1998 | Aggarwal et al. |
| 5,798,554 A | 8/1998 | Grimaldi et al. |
| 5,817,307 A | 10/1998 | Cummins |
| 5,824,701 A | 10/1998 | Greenwald et al. |
| 5,840,854 A | 11/1998 | Hellstrom et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,056,973 A | 5/2000 | Allen et al. |
| 6,077,499 A | 6/2000 | Griffiths et al. |
| 6,096,289 A | 8/2000 | Goldenberg |
| 6,156,754 A | 12/2000 | Lerchen et al. |
| 6,165,440 A | 12/2000 | Esenaliev |
| 6,180,377 B1 | 1/2001 | Morgan et al. |
| 6,183,744 B1 | 2/2001 | Goldenberg |
| 6,187,287 B1 | 2/2001 | Leung et al. |
| 6,201,104 B1 | 3/2001 | MacDonald et al. |
| 6,214,345 B1 | 4/2001 | Firestone et al. |
| 6,254,868 B1 | 7/2001 | Leung et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |
| 6,530,944 B2 | 3/2003 | West et al. |
| 6,558,669 B1 | 5/2003 | Govindan et al. |
| 6,562,318 B1 | 5/2003 | Filler |
| 6,653,104 B2 | 11/2003 | Goldenberg et al. |
| 6,716,821 B2 | 4/2004 | Zhao et al. |
| 6,824,780 B1 | 11/2004 | Devaux et al. |
| 6,962,702 B2 | 11/2005 | Hansen et al. |
| 7,018,809 B1 | 3/2006 | Carter |
| 7,074,403 B1 | 7/2006 | Goldenberg et al. |
| 7,122,636 B1 | 10/2006 | Hsei et al. |
| 7,151,164 B2 | 12/2006 | Hansen et al. |
| 7,238,785 B2 | 7/2007 | Govindan et al. |
| 7,288,249 B2 | 10/2007 | Carter et al. |
| 7,312,318 B2 | 12/2007 | Hansen et al. |
| 7,387,779 B2 | 6/2008 | Kalluri |
| 7,420,040 B2 | 9/2008 | Young et al. |
| 7,420,041 B2 | 9/2008 | Young et al. |
| 7,585,491 B2 | 9/2009 | Govindan et al. |
| 7,591,994 B2 | 9/2009 | Govindan et al. |
| 7,772,373 B2 | 8/2010 | Hansen et al. |
| 7,820,161 B1 | 10/2010 | Curd et al. |
| 7,910,103 B2 | 3/2011 | Goldenberg |
| 7,931,903 B2 | 4/2011 | Hansen et al. |
| 7,999,083 B2 | 8/2011 | Govindan et al. |
| 8,080,250 B1 | 12/2011 | Govindan et al. |
| 8,119,101 B2 | 2/2012 | Byrd et al. |
| 8,268,317 B2 | 9/2012 | Govindan et al. |
| 8,268,319 B2 | 9/2012 | Govindan et al. |
| 8,309,094 B2 | 11/2012 | Gerber et al. |
| 8,420,086 B2 | 4/2013 | Govindan et al. |
| 8,425,912 B2 | 4/2013 | Govindan et al. |
| 8,586,049 B2 | 11/2013 | Gerber et al. |
| 8,617,558 B2 | 12/2013 | Govindan et al. |
| 8,658,773 B2 | 2/2014 | Zeng et al. |
| 8,715,662 B2 | 5/2014 | Alberti |
| 8,741,300 B2 | 6/2014 | Govindan et al. |
| 8,759,496 B2 | 6/2014 | Govindan et al. |
| 8,834,886 B2 | 9/2014 | Govindan et al. |
| 8,871,908 B2 | 10/2014 | Liu et al. |
| 8,877,202 B2 | 11/2014 | Govindan et al. |
| 8,877,901 B2 | 11/2014 | Govindan et al. |
| 9,180,205 B2 | 11/2015 | Zeng et al. |
| 2001/0034363 A1 | 10/2001 | Li et al. |
| 2002/0018749 A1 | 2/2002 | Hudson et al. |
| 2003/0103979 A1 | 6/2003 | Leung et al. |
| 2003/0133972 A1 | 7/2003 | Danthi et al. |
| 2003/0162709 A1 | 8/2003 | Rossi et al. |
| 2004/0001838 A1 | 1/2004 | Zhao et al. |
| 2004/0076683 A1 | 4/2004 | Hoarau et al. |
| 2006/0142506 A1 | 6/2006 | Breitenkamp et al. |
| 2006/0193865 A1 | 8/2006 | Govindan et al. |
| 2007/0212350 A1 | 9/2007 | Govindan et al. |
| 2008/0166363 A1 | 7/2008 | Govindan et al. |
| 2010/0104589 A1* | 4/2010 | Govindan ........ A61K 47/48215 424/181.1 |
| 2011/0160159 A1 | 6/2011 | Ryan |
| 2011/0256053 A1 | 10/2011 | Chang et al. |
| 2011/0274704 A1 | 11/2011 | Chang et al. |
| 2011/0305631 A1 | 12/2011 | Govindan et al. |
| 2012/0052076 A1 | 3/2012 | Alberti |
| 2012/0082617 A1 | 4/2012 | Govindan et al. |
| 2012/0237518 A1 | 9/2012 | Yamaguchi et al. |
| 2012/0328564 A1 | 12/2012 | Govindan et al. |
| 2013/0089872 A1 | 4/2013 | Nakamura et al. |
| 2013/0090458 A1 | 4/2013 | Govindan et al. |
| 2013/0122020 A1 | 5/2013 | Liu et al. |
| 2013/0177526 A1 | 7/2013 | Govindan et al. |
| 2013/0216561 A1 | 8/2013 | Govindan et al. |
| 2014/0004078 A1 | 1/2014 | Govindan et al. |
| 2014/0058067 A1 | 2/2014 | Govindan et al. |
| 2014/0170063 A1 | 6/2014 | Govindan et al. |
| 2014/0178294 A1 | 6/2014 | Zeng et al. |
| 2014/0219914 A1 | 8/2014 | Govindan et al. |
| 2014/0227180 A1 | 8/2014 | Govindan et al. |
| 2014/0286860 A1 | 9/2014 | Govindan et al. |
| 2014/0357659 A1 | 12/2014 | Hoch et al. |
| 2016/0032008 A1 | 2/2016 | Zeng et al. |

FOREIGN PATENT DOCUMENTS

| | | |
|---|---|---|
| EP | 0306943 | 3/1989 |
| EP | 0332865 | 9/1989 |
| EP | 0510949 | 10/1992 |
| WO | 90/09196 | 8/1990 |
| WO | 91/11465 | 8/1991 |
| WO | 91/13974 | 9/1991 |
| WO | 94/27638 | 12/1994 |
| WO | 95/05468 | 2/1995 |
| WO | 9509917 | 4/1995 |
| WO | 96/04925 | 2/1996 |
| WO | 98/04281 | 2/1998 |
| WO | 98/12227 | 3/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 00/69914 | 11/2000 |
| WO | 0074718 | 12/2000 |
| WO | 0076551 | 12/2000 |
| WO | 0124763 | 4/2001 |
| WO | 2004054622 | 7/2004 |
| WO | 2007112193 | 10/2007 |
| WO | 2007123995 | 11/2007 |
| WO | 2009100194 | 8/2009 |
| WO | 2010089782 | 8/2010 |
| WO | 2010093395 | 8/2010 |
| WO | 2010111388 | 9/2010 |
| WO | 2012151199 | 11/2012 |
| WO | 2014092804 | 6/2014 |
| WO | 2015047510 | 4/2015 |

OTHER PUBLICATIONS

Alix-Panabieres et al., "Circulating tumor cells: liquid biopsy of cancer", Clin Chem. Jan. 2013;59(1):110-8.

Baeuerle et al., "EpCAM (CD326) finding its role in cancer", Br J Cancer. Feb. 12, 2007;96(3):417-23.

Bignotti et al., "Trop-2 protein overexpression is an independent marker for predicting disease recurrence in endometrioid endometrial carcinoma", BMC Clin Pathol. Nov. 14, 2012;12:22.

(56) References Cited

OTHER PUBLICATIONS

Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31, Epub May 8, 2015.
Chang et al., "Ranpirnase (frog RNase) targeted with a humanized, internalizing, anti-Trop-2 antibody has potent cytotoxicity against diverse epithelial cancer cells", Mol Cancer Ther. Aug. 2010;9(8):2276-86.
Chen et al., "Increased expression of Trop2 correlates with poor survival in extranodal NK/T cell lymphoma, nasal type", Virchows Arch. Nov. 2013;463(5):713-9.
Cubas et al., "Trop2: a possible therapeutic target for late stage epithelial carcinomas", Biochim Biophys Acta. Dec. 2009;1796(2):309-14.
Cubas et al., "Trop2 expression contributes to tumor pathogenesis by activating the ERK MAPK pathway", Mol Cancer. Sep. 21, 2010;9:253.
Fang et al., "Different effects of ERβ and TROP2 expression in Chinese patients with early-stage colon cancer", Tumour Biol. Dec. 2012;33(6):2227-35.
Farivar et al., "Nano—drug Delivery of Apoptosis Activator 2 to AGS Cells by Liposomes Conjugated with Anti-TROP2 Antibody", N Am J Med Sci. Nov. 2012;4(11):582-5.
Friedman et al., "BR96 sFv-PE40, a potent single-chain immunotoxin that selectively kills carcinoma cells", Cancer Res. Jan. 15, 1993;53(2):334-9.
Goldenberg et al., "Trop-2 is a novel target for solid cancer therapy with sacituzumab govitecan (IMMU-132), an antibody-drug conjugate (ADC)", Oncotarget. Jun. 18, 2015 [Epub ahead of print].
Gupta et al., "ApoStream™, a new dielectrophoretic device for antibody independent isolation and recovery of viable cancer cells from blood", Biomicrofluidics. Jun. 27, 2012;6(2)24133.
Harb et al., "Mutational Analysis of Circulating Tumor Cells Using a Novel Microfluidic Collection Device and qPCR Assay", Transl Oncol. Oct. 1, 2013;6(5):528-38.
Ikeda et al., "Pr1E11, a novel anti-TROP-2 antibody isolated by adenovirus-based antibody screening, recognizes a unique epitope", Biochem Biophys Res Commun. Mar. 20, 2015;458(4):877-82.
Joosse et al., "Biology, detection, and clinical implications of circulating tumor cells", EMBO Mol Med. Nov. 14, 2014;7(1):1-11.
Kapoor, S., "TROP2 expression and its evolving role in tumor pathogenesis in systemic tumors", Tumour Biol. Jun. 2013;34(3):1967-8.
Krisfinamurthy et al., "Discordance in HER2 gene amplification in circulating and disseminated tumor cells in patients with operable breast cancer", Cancer Med. Apr. 2013;2(2):226-33.
Lin et al., "Continuous labeling of circulating tumor cells with microbeads using a vortex micromixer for highly selective isolation", Biosens Bioelectron. Feb. 15, 2013;40(1):63-7.
Lin et al., "Significantly upregulated TACSTD2 and Cyclin D1 correlate with poor prognosis of invasive ductal breast cancer", Exp Mol Pathol. Feb. 2013;94(1):73-8.
Lin et al., "A novel human Fab antibody for Trop2 inhibits breast cancer growth in vitro and in vivo", Int J Cancer. Mar. 1, 2014;134(5):1239-49.
Lipinski et al., "Human trophoblast cell-surface antigens defined by monoclonal antibodies", Proc Natl Acad Sci U S A. Aug. 1981;78(8):5147-50.
Liu et al., "Overexpression of TROP2 predicts poor prognosis of patients with cervical cancer and promotes the proliferation and invasion of cervical cancer cells by regulating ERK signaling pathway", PLoS One. Sep. 27, 2013;8(9): e75864.
Liu et al., "Trop-2-targeting tetrakis-ranpirnase has potent antitumor activity against triple-negative breast cancer", Mol Cancer. Mar. 10, 2014;13:53.

Magbanua et al., "Circulating tumor cell analysis in metastatic triple-negative breast cancers", Clin Cancer Res. Mar. 1, 2015;21(5):1098-105.
Mykolajczyk et al., "Detection of EpCAM-Negative and Cytokeratin-Negative Circulating Tumor Cells in Peripheral Blood", J Oncol. 2011;2011:252361.
Ning et al., "TROP2 correlates with microvessel density and poor prognosis in hilar cholangiocarcinoma", J Gastrointest Surg. Feb. 2013;17(2):360-8.
Ning et al., "TROP2 expression and its correlation with tumor proliferation and angiogenesis in human gliomas", Neurol Sci. Oct. 2013;34(10):1745-50.
Pak et al., "Significance of EpCAM and TROP2 expression in non-small cell lung cancer", World J Surg Oncol. Apr. 6, 2012;10:53.
Pecot et al., "A novel platform for detection of CK+ and CK-CTCs", Cancer Discov. Dec. 2011;1(7):580-6.
Powell et al., "Single cell profiling of circulating tumor cells: transcriptional heterogeneity and diversity from breast cancer cell lines", PLoS One. 2012;7(5):e33788.
Sapra et al., "Long-term tumor regression induced by an antibody-drug conjugate that targets 5T4, an oncofetal antigen expressed on tumor-initiating cells", Mol Cancer Ther. Jan. 2013;12(1):38-47.
Saucedo-Zeni et al., "A novel method for the in vivo isolation of circulating tumor cells from peripheral blood of cancer patients using a functionalized and structured medical wire", Int J Oncol. Oct. 2012;41(4):1241-50.
Sharkey et al., "Enhanced Delivery of SN-38 to Human Tumor Xenografts with an Anti-Trop-2-Sn-38 Antibody Conjugate (Sacituzumab Govitecan)", Clin Cancer Res. Jun. 23, 2015. pii: clincanres.0670.2015. [Epub ahead of print].
Shor et al., "Enhanced Antitumor Activity of an Anti-5T4 Antibody-Drug Conjugate in Combination with PI3K/mTOR Inhibitors or Taxanes", Clin Cancer Res. Jan. 15, 2016;22(2):383-94.
Shvartsur et al., "Trop2 and its overexpression in cancers: regulation and clinical/therapeutic implications", Genes Cancer. Mar. 2015;6(3-4):84-105.
Stepan et al., "Expression of Trop2 cell surface glycoprotein in normal and tumor tissues: potential implications as a cancer therapeutic target", J Histochem Cytochem. Jul. 2011;59(7):701-10.
Stoyanova et al., "Regulated proteolysis of Trop2 drives epithelial hyperplasia and stem cell self-renewal via β-catenin signaling", Genes Dev. Oct. 15, 2012;26(20):2271-85.
Trerotola et al., "Letter to the editor: efficacy and safety of anti-Trop antibodies, R. Cubas, M. Li, C. Chen and Q. Yao, Biochim Biophys Acta 1796 (2009) 309-1", Biochim Biophys Acta. Apr. 2010;1805(2):119-20.
Truini et al., "Clinical Applications of Circulating Tumor Cells in Lung Cancer Patients by CellSearch System", Front Oncol. Sep. 4, 2014;4:242.
Tsukahara et al., "TROP2 expressed in the trunk of the ureteric duct regulates branching morphogenesis during kidney development", PLoS One. 2011;6(12):e28607.
Varughese et al., "Cervical carcinomas overexpress human trophoblast cell-surface marker (Trop-2) and are highly sensitive to immunotherapy with hRS7, a humanized monoclonal anti-Trop-2 antibody", Am J Obstet Gynecol. Dec. 2011;205(6):567.e1-7.
Vidmar et al., "Biochemical and preliminary X-ray characterization of the tumor-associated calcium signal transducer 2 (Trop2) ectodomain", Protein Expr Purif. Sep. 2013;91(1):69-76.
Wang et al., "Identification of Trop-2 as an oncogene and an attractive therapeutic target in colon cancers", Mol Cancer Ther. Feb. 2008;7(2):280-5.
Wang et al., "Loss of Trop2 promotes carcinogenesis and features of epithelial to mesenchymal transition in squamous cell carcinoma", Mol Cancer Res. Dec. 2011;9(12):1686-95.
Wang et al., "Detection of circulating tumor cell-specific markers in breast cancer patients using the quantitative RT-PCR assay", Int J Clin Oncol. Oct. 2015;20(5):878-90.
Winer-Jones et al., "Circulating tumor cells: clinically relevant molecular access based on a novel CTC flow cell", PLoS One. Jan. 29, 2014;9(1):e86717.

(56) References Cited

OTHER PUBLICATIONS

Wu et al., "Potential therapeutic target and independent prognostic marker of TROP2 in laryngeal squamous cell carcinoma", Head Neck. Oct. 2013;35(10):1373-8.
Alberts et al., Molecular Biology of the Cell, 3rd Ed., pp. 1216-1218, Garland Publishing, Inc. (1994).
Basu et al., "The epithelial/carcinoma antigen EGP-1, recognized by monoclonal antibody RS7-3G11, is phosphorylated on serine 303" Int. J. Cancer 62(4):472-479 (1995).
Bendig et al., "Humanization of Rodent Monoclonal Antibodies by CDR Grafting" Methods: A Companion to Methods in Enzymology 8:83-93 (1995).
Carter et al., Chemotherapy of Cancer; 2nd Edition; John Wiley & Sons, New York, 1981; Appendix C.
Chari et al., "Immunoconjugates Containing Novel Maytansinoids: Promising Anticancer Drugs" Cancer Res. Jan. 1, 1992;52(1):127-31.
El Sewedy et al., "Cloning of the murine TROP2 gene: conservation of a PIP2-binding sequence in the cytoplasmic domain of TROP-2", Int J Cancer. Jan. 19, 1998;75(2):324-30.
Frolich et al., "The anti-CD74 humanized monoclonal antibody, milatuzumab, which targets the invariant chain of MHC II complexes, alters B-cell proliferation, migration, and adhesion molecule expression", Arthritis Res Ther. Mar. 9, 2012;14(2):R54.
Govindan et al., "Preclinical therapy of breast cancer with a radioiodinated humanized anti-EGP-1 monoclonal antibody: advantage of a residualizing iodine radiolabel", Breast Cancer Res Treat. Mar. 2004;84(2):173-82.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Hatzakis et al., "Synthesis and single enzyme activity of a clicked lipase-BSA hetero-dimer" Chem. Commun., 2006, 2012-2014.
Heindel et al., "A Novel Heterobifunctional Linker for Formyl to Thiol Coupling" Bioconjugate Chem. 1991, 2, 427-430.
Huang et al., "The Rana catesbeiana rcr Gene Encoding a Cytotoxic Ribonuclease" J. Biol. Chem. 273(11):6395-6401 (1998).
Jiang et al., "A Novel Peptide Isolated from a Phage Display Peptide Library with Trastuzumab Can Mimic Antigen Epitope of HER-2", J. Biol. Chem. Feb. 2005;280(6):4656-4662.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Krontiris and Capizzi, Internal Medicine, Chapters 71-72, pp. 699-729; 4th Edition, Jay Stein (Ed.), Elsevier Science, 1994.
Leung et al., "Chimerization of LL2, a Rapidly Internalizing Antibody Specific for B Cell Lymphoma" Hybridoma 13(6):469-476 (1994).
Miller et al., "Development of Taxoids with Enhanced Toxicity and Solubility" Poster Presentation, 224th ACS Nat. Meeting, Aug. 18-22, 2002, Boston, MA.
Moon et al., "Antibody Conjugates of 7-Ethyl-10-hydroxycamptothecin (SN-38) for Targeted Cancer Chemotherapy" J. Med. Chem. 2008, 51, 6916-6926.
Morrison et al., "Chimeric human antibody molecules: Mouse antigen-binding domains with human constant region domains" Proc. Natl. Acad. Sci, USA 81:6851-6855 (1984).
Newton et al., "Potent and specific antitumor effects of an anti-CD22-targeted cytotoxic ribonuclease: potential for the treatment of non-Hodgkin lymphoma" Blood, 97(2):528-35 (2001).
Paul, W., Fundamental Immunology, 3rd Ed., p. 242; pp. 292-295, Raven Press, New York (1993).
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Qu et al., "Humanization of Immu31, an α-Fetoprotein-specific Antibody" Clin. Cancer Res. 5(10 Suppl):3094s-3100s (1999).
Reddy et al., "Elimination of Fc Receptor-Dependent Effector Functions of a Modified IgG4 Monoclonal Antibody to Human CD4", J. Immunol. 164:1925-1933 (2000).
Ripani et al., "Human Trop-2 is a tumor-associated calcium signal transducer", Int J Cancer. May 29, 1998;76(5):671-6.
Rowlinson-Busza et al., "Targeted delivery of biologic and other antineoplastic agents" Curr. Opin. Oncol. Dec. 1992;4(6):1142-1148.
Rudikoff et al., "Single amino acid substitution altering antigen-binding specificity" Proc. Natl. Acad. Sci. USA 79:1979-1983 (1982).
Schoonjans et al., "FAB chains as an Efficient Heterodimerization Scaffold for the Production of Recombinant Bispecific and Trispecific Antibody Derivatives" J. Immunol. 165(12):7050-7057 (2000).
Shih et al., "The Processing and Fate of Antibodies and Their Radiolabels Bound to the Surface of Tumor Cells in Vitro: A Comparison of Nine Radiolabels" J. Nucl. Med. 35(5):899-908 (1994).
Shih et al., "In Vitro and in Vivo Reactivity of an Internalizing Antibody, RS7, with Human Breast Cancer" Cancer Res. 55(23 Suppl.):5857s-5863s (1995).
Stancovski et al., "Mechanistic aspects of the opposing effects of monoclonal antibodies to the ERBB2 receptor on tumor growth", Proc Natl Acad Sci U S A. Oct. 1, 1991;88(19):8691-5.
Stein et al., "Therapy of a Breast Cancer Xenograft Using Humanized RS7 Labeled with Residualizing Iodine" Proc. Am. Assoc. Cancer Res. vol. 43, pp. 88-89, Mar. 2002 (Abstract).
Stein et al., "Comparative Biodistribution and Radioimmunotherapy of Monoclonal Antibody RS7 and its F(ab')2 in Nude Mice Bearing Human Tumor Xenografts" Cancer 73:816-823 (1994).
Stein et al., "Effects of Radiolabeling Monoclonal Antibodies with a Residualizing Iodine Radiolabel on the Accretion of Radioisotope in Tumors" Cancer Res. 55(14):3132-3139 (1995).
Stein et al., "Specificity and properties of MAb RS7-3G11 and the antigen defined by this pancarcinoma monoclonal antibody" Int. J. Cancer 55(6):938-946 (1993).
Stein et al., "Characterization of cluster 13: the epithelial/carcinoma antigen recognized by MAb RS7" Int. J. Cancer 57(S8):98-102 (1994).
Stein et al., "Murine Monoclonal Antibodies Raised against Human Non-Small Cell Carcinoma of the Lung: Specificity and Tumor Targeting" Cancer Res. 50(4):1330-1336 (1990).
Stein et al., "Radioimmunotherapy of a human lung cancer xenograft with monoclonal antibody RS7: evaluation of (177)Lu and comparison of its efficacy with that of (90)Y and residualizing (131)I", J Nucl Med. Jun. 2001;42(6):967-74.
Stein et al., "Improved iodine radiolabels for monoclonal antibody therapy", Cancer Res. Jan. 1, 2003;63(1):111-8.
Stein et al., "Successful therapy of a human lung cancer xenograft using MAb RS7 labeled with residualizing radioiodine", Crit Rev Oncol Hematol. Jul.-Aug. 2001;39(1-2):173-80.
Stein et al., "Targeting human cancer xenografts with monoclonal antibodies labeled using radioiodinated, diethylenetriaminepentaacetic acid-appended peptides", Clin Cancer Res. Oct. 1999;5(10 Suppl):3079s-3087s.
Stein et al., "Advantage of yttrium-90-labeled over iodine-131-labeled monoclonal antibodies in the treatment of a human lung carcinoma xenograft", Cancer Dec. 15, 1997;80(12 Suppl):2636-41.
Steinfeld et al., "Epratuzumab (humanised anti-CD22 antibody) in autoimmune diseases", Expert Opin Biol Ther. Sep. 2006;6(9):943-9.
Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).

(56) References Cited

OTHER PUBLICATIONS

Suzawa et al., "Enhanced tumor cell selectivity of adriamycin-monoclonal antibody conjugate via a poly(ethylene glycol)-based cleavable linker" J. Control. Release 79:229-242 (2002).

Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.

Walker et al., "Synthesis of an Immunoconjugate of Camptothecin" Bioorg. Med. Chem. Lett. 12(2):217-219 (2002).

Yazawa et al., "Immunotherapy using unconjugated CD19 monoclonal antibodies in animal models for B lymphocyte malignancies and autoimmune disease", Proc Natl Acad Sci U S A. Oct. 18, 2005;102(42):15178-83.

Bardia et al., "Safety and efficacy of anti-Trop-2 antibody drug conjugate, sacituzumab govitecan (IMMU-132), in heavily pretreated patients with TNBC", Poster presented at San Antonio Breast Cancer Symposium, Dec. 10, 2015, San Antonio, TX.

Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.

Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.

Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference On Lung Cancer (WCLC), Sep. 7, 2015, Denver, CO.

Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.

Cardillo et al., "Combining an anti-Trop-2 antibody-SN-38 conjugate (sacituzumab govitecan) with microtubule inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.

Cardillo et al., "Synthetic lethality in TNBC mediated by an anti-Trop-2 antibody-drug conjugate, sacituzumab govitecan (IMMU-132), when combined with paclitaxel or the PARP inhibitor, olaparib", Poster presented at San Antonio Breast Cancer Symposium, Dec. 10, 2015, San Antonio, TX.

Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.

Goldenberg et al., Tolerability in mice, monkeys, and rabbits of new antibody (MAb)-drug (SN-38) Immunoconjugates. Proc. Amer. Assoc. Cancer Res. 102nd Annual Meeting, 52: 865 (Abstr. #3619), 2011.

Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.

Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.

Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.

Govindan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.

Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.

Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.

Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.

Liu et al., "Novel immunoRNases comprising multiple copies of ranpirnase display potent cytotoxicity in human breast cancer cell lines expressing Trop-2", Proc. Amer. Assoc. Cancer Res. 103rd Annual Meeting, 53: 1124 (Abstr. #4636), 2012.

Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.

Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR) Special Conference on Pancreatic Cancer:Innovations in Research and Treatment, Abstr. #B99, May 18-21, 2014.

Shih et al., "Radioimmunodetection and radioimmunotherapy of xenografted human breast cancer with monoclonal antibody RS7", J. Immunother. 16: 169 (Abstr. #85), 1994.

Starodub et al., "Advanced solid cancer therapy with a novel antibody-drug conjugate (ADC), sacituzumab govitecan (IMMU-132): key preclinical and clinical results", Abstract CT236. Presented at American Association for Cancer Research (AACR) 2015 Annual Meeting, Philadelphia, PA, Apr. 20, 2015.

Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.

Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.

Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.

Stein et al., "Radioimmunotherapy of lung cancer with MAb RS7-3G11", Proc. Amer. Assoc. Cancer Res. 33: 318 (Abstr. #1897), 1992.

Stein et al., "Radioimmunotherapy with MAb RS7-3G11 in an animal model", Antib. Immunoconj. Radiopharm. 5: 358 (Abstr. #100), 1992.

Stein et al., "Assessment of combined radioimmunotherapy and chemotherapy for treatment of medullary thyroid cancer", Clin Cancer Res. 5(10 Suppl):3199s-206s, 1999.

Stein et al., Characterization of the epithelial/carcinoma antigen recognized by MAb RS7. Proc. Amer. Assoc. Cancer Res. 35: 501 (Abstr. #2986), 1994.

Stein et al., A novel tumor-associated antigen defined by MAb RS7-3G11: Characterization and internalization properties. Proc. Amer. Assoc. Cancer Res. 33: 341, 1992.

(56) References Cited

OTHER PUBLICATIONS

Stein et al., "Targeting and therapy of human non small cell carcinoma of the lung xenografts using 131 I labeled monoclonal antibody RS7 3G11", Proc. Amer. Assoc. Cancer Res. 32: 260, 1991.
Van Rij et al., "Imaging of prostate cancer with immuno-PET and immuno-SPECT using a radiolabeled anti-EGP-1 monoclonal antibody", J Nucl Med. 52(10):1601-7, 2011.
Van Rij et al., "Pretargeting of prostate cancer with an internalizing anti-EGP-1 x anti-HSG bispecific antibody", Annual Congress of the European Association of Nuclear Medicine, Birmingham, UK, Eur J Nucl Med Mol Imaging 38 (Suppl 2):S212 (Abstr. #OP582), 2011.
Vanama et al., Construction, characterization, and mammalian expression of an immunotoxin consisting of ranpimase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.
Baum et al., "Initial clinical results with technetium-99m-labeled LL2 monoclonal antibody fragment in the radioimmunodetection of B-cell lymphomas", Cancer Feb. 1, 1994;73(3 Suppl):896-9.
Beers et al., The Merck Manual of Diagnosis and Therapy, Ch. 180, p. 1474-1476; 17th Ed., Whitehouse Station, NJ, Merck Research Labs (1999).
Belisle et al., "Epitope specificity of the anti-B-cell lymphoma monoclonal antibody, LL2", Proc Am Assoc Cancer Res 1993; 34:481, Abstr #2873.
Bendig, M., "Humanization of Rodent Monoclonal Antibodies by CDR Grafting", Academic Press Inc., New York, NY, vol. 8, (1995), pp. 83-93.
Bhat et al., "Human antilipid A monoclonal antibodies bind to human B cells and the i antigen on cord red blood cells", J Immunol. Nov. 1, 1993;151(9):5011-21.
Carter et al., "Humanization of an anti-p185HER2 antibody for human cancer therapy", Proc. Natl. Acad. Sci. USA 89(10):4285-9 (1992).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Coloma et al., "Design and production of novel tetravalent bispecific antibodies", Nat. Biotechnol. 15(2):159-63 (1997).
Dillon et al., "Use of Polymerase Chain Reaction for the Rapid Construction of Synthetic Genes", Methods in Molecular Biology, vol. 15: PCR Protocols: Current Methods and Applications, White (Ed.), pp. 263-268, Humana Press, Inc. (1993).
Ellis et al., "Engineered anti-CD38 monoclonal antibodies for immunotherapy of multiple myeloma", J Immunol. Jul. 15, 1995;155(2):925-37.
Flavell et al., "Systemic therapy with 3BIT, a triple combination cocktail of anti-CD19, -CD22, and -CD38-saporin immunotoxins, is curative of human B-cell lymphoma in severe combined immuno-deficient mice", Cancer Res. 57:4824-9 (1997).
Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.
French et al., "Response of B-cell lymphoma to a combination of bispecific antibodies and saporin", Leuk. Res. 20(7):607-17 (1996).
Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Goldenberg et al., "Targeting, dosimetry, and radioimmunotherapy of B-cell lymphomas with iodine-131-labeled LL2 monoclonal antibody", J Clin Oncol. Apr. 1991;9(4):548-64.
Goldenberg, D. M. "New Developments in Monoclonal Antibodies for Cancer Detection and Therapy", CA Cancer J. Clin. 44(1):43-64 (1994).
Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and In Combination with Veltuzumab, a Humanized Anti-CD20 MAb", Blood (ASH Annual Meeting Abstracts) 2010 116: Abstract 3941.
Gondo et al., "HLA class II antigen associated invariant chain gene expression in malignant lymphoma", Br. J. Haematol. 67(4):413-7 (1987).
Green et al., "Antigen-specific human monoclonal antibodies from mice engineered with human Ig heavy and light chain YACs", Nature Genetics 7:13-21 (1994).
Gussow et al., "Humanization of monoclonal antibodies", Methods Enzymol. 1991;203:99-121.
Hansen et al., "Internalization and catabolism of radiolabelled antibodies to the MHC class-II invariant chain by B-cell lymphomas", Biochem. J. 1996, 320:293-300.
Hashida et al., "More useful maleimide compounds for the conjugation of Fab' to horseradish peroxidase through thiol groups in the hinge", J Appl Biochem. Feb.-Apr. 1984;6(1-2):56-63.
Hekman et al. "Initial experience with treatment of human B cell lymphoma with anti-CD19 monoclonal antibody", Cancer Immunol. Immunother. 1991;32(6):364-72.
Hess et al., "Specificity of effector T lymphocytes in autologous graft-versus-host disease: role of the major histocompatibility complex class II invariant chain peptide", Blood 89(6):2203-9 (1997).
Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.
IMURAN patient information leaflet, GlaxoSmithKline 7076598/5093, Oct. 2004.
Inaoki et al., "CD19-regulated signaling thresholds control peripheral tolerance and autoantibody production in B lymphocytes", J Exp Med. Dec. 1, 1997;186(11):1923-31.
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-2,D22 monoclonal antibody", Cancer Res. 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiener et al., "Stimulation of CD40 with purified soluble gp39 induces proinflammatory responses in human monocytes", J Immunol. Nov. 15, 1995;155(10):4917-25.
Kiesel et al., "Removal of cells from a malignant B-cell line from bone marrow with immunomagnetic beads and with complement and immunoglobulin switch variant mediated cytolysis", Leuk. Res. 11(12):1119-25 (1987).
Kohler et aL, "Continuous cultures of fused cells secreting antibody of predefined specificity", Nature 256:495-7 (1975).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).

(56) References Cited

OTHER PUBLICATIONS

Leung et al., "Chimerization and humanization of a B-cell Lymphoma specific antibody, LL2", Proc Am Assoc Cancer Res 1993; 34:481, Abstr #2872.
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52(8):1701-4 (1999).
Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L. "Immunotherapy for non-Hodgkin's lymphoma", Curr. Opin. Oncol. 8(5):353-9 (1996).
Losman et al., "Baboon anti-idiotype antibodies mimic a carcinoembryonic antigen epitope", Int J Cancer. Aug. 15, 1990;46(2):310-4.
Lundberg, B. "Preparation of drug-carrier emulsions stabilized with phosphatidylcholine-surfactant mixtures", J. Pharm. Sci. 83(1):72-5 (1994).
Lundberg et al., "Submicron lipid emulsions containing amphipathic polyethylene glycol for use as drug-carvers with prolonged circulation time", Int. J. Pharm. 134:119-127 (1996).
Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11(9):1936-47.
Beckman et al., "Antibody constructs in cancer therapy: protein engineering strategies to improve exposure in solid tumors", Cancer. Jan. 15, 2007;109(2):170-9.
Berenbaum, MC., "Synergy, additivism and antagonism in immunosuppression. A critical review", Clin Exp Immunol. Apr. 1977;28(1):1-18.
Berenbaum, MC., "What is synergy?", Pharmacol Rev. Jun. 1989;41(2):93-141.
Cespedes et al, "Mouse models in oncogenesis and cancer therapy", Clin Transl Oncol. May 2006;8(5):318-29.
Dennis, C., "Cancer: off by a whisker", Nature. Aug. 17, 2006;442(7104):739-41.
Foran, JM., "Antibody-based therapy of non-Hodgkin's lymphoma", Best Pract Res Clin Haematol. Sep. 2002;15(3):449-65.
Fujimori et al., "A modeling analysis of monoclonal antibody percolation through tumors: a binding-site barrier", J Nucl Med. Jul. 1990;31(7):1191-8.
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.
Mason et al., "Value of monoclonal anti-CD22 (p135) antibodies for the detection of normal and neoplastic B lymphoid cells", Blood. Mar. 1987;69(3):836-40.
Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).

Morrison et al., "Chimeric human antibody molecules: mouse antigen-binding domains with human constant region domains", Proc Natl Acad Sci USA Nov. 1984;81(21):6851-5.
Murthy et al., "Lymphoma imaging with a new technetium-99m labelled antibody, LL2", Eur J Nucl Med. 1992;19(6):394-401.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human lymphoma", Cancer Res. 49(16):4568-77 (1989).
Perrota et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates", Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).
Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86(24):10029-33.
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudnick et al., "Affinity and avidity in antibody-based tumor targeting", Cancer Biother Radiopharm. Apr. 2009;24(2):155-61.
Saltzman et al., "Transport rates of proteins in porous materials with known microgeometry", Biophys. J. 55(1)163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sherwood et al., "Controlled antibody delivery systems", Biotechnology 10(11):1446-9 (1992).
Shih et al., "Internalization and intracellular processing of an anti-B-cell lymphoma monoclonal antibody, LL2", Int J Cancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).

(56) References Cited

OTHER PUBLICATIONS

Tallarida, R.J., Drug Synergism and Dose Effect Analysis, Ed. Chapman & Hall, 2000, pp. 1-8; 10-13; 57-71.

Taylor et al., "Human immunoglobulin transgenes undergo rearrangement, somatic mutation and class switching in mice that lack endogenous IgM", Int Immunol. Apr. 1994;6(4):579-91.

Theocharis et al., "Characterization of in vivo mutated T cell clones from patients with systemic lupus erythematosus", Clin. Immunol. Immunopathol. 74(2):135-42 (1995).

Tsang et al.,"Reactive oxygen species mediate doxorubicin induced p53-independent apoptosis", Life Sci. Sep. 5, 2003;73(16):2047-58.

Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).

Wilson et al., "cDNA cloning of the B cell membrane protein CD22: a mediator of B-B cell interactions", J Exp Med. Jan. 1, 1991;173(1):137-46.

Wilson et al., "Genomic structure and chromosomal mapping of the human CD22 gene", J Immunol. Jun. 1, 1993;150(11):5013-24.

Wosnik et al., "Rapid construction of large synthetic genes: total chemical synthesis of two different versions of the bovine prochymosin gene", Gene. 1987;60(1):115-27.

Wurflein et al., "Evaluating antibodies for their capacity to induce cell-mediated lysis of malignant B cells", Cancer Res. Jul. 15, 1998;58(14):3051-8.

De Albuquerque et al., "Multimarker Analysis of Circulating Tumor Cells in Peripheral Blood of Metastatic Breast Cancer Patients: A Step Forward in Personalized Medicine", Breast Care (Basel). Feb. 2012;7(1):7-12.

Kallioniemi et al., "Gene Copy Number Analysis by Fluorescence in Situ Hybridization and Comparative Genomic Hybridization", Methods. Feb. 1996;9(1):113-21.

Loberg et al., "Detection and isolation of circulating tumor cells in urologic cancers: a review", Neoplasia. Jul.-Aug. 2004;6(4):302-9.

Bardia et al., "Therapy of refractory/relapsed metastatic triple-negative breast cancer (TNBC) with an anti-Trop-2-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibary.asco.org/content/150673-156.

Bardia et al., "IMMU-132, a new antibody-drug conjugate (ADC) against Trop-2, as a novel therapeutic for patients with relapsed/refractory, metastatic, triple-negative breast cancer (TNBC): Results from Phase I/II clinical trial (NCT01631552)", Poster, San Antonio Breast Cancer Symposium, Dec. 9-13, 2014.

Bennouna et al., "Therapeutic strategies for colorectal cancer in Europe and the United States: focus on chemotherapy for advanced colorectal cancer" Int. J. Clin. Oncol. (2002) 7:236-244.

Burkard et al., "Validating cancer drug targets through chemical genetics", Biochim Biophys Acta. Dec. 2010;1806(2):251-7.

Burke et al., "Design, synthesis, and biological evaluation of antibody-drug conjugates comprised of potent camptothecin analogues", Bioconjug Chem. Jun. 2009;20(6):1242-50.

Burnham et al., "Invasion of HeLa cells by group B streptococcus requires the phosphoinositide-3-kinase signalling pathway and modulates phosphorylation of host-cell Akt and glycogen synthase kinase-3", Microbiology. Dec. 2007;153(Pt 12):4240-52.

Cao et al., "Bispecific Antibodies as Novel Bioconjugates" Bioconj. Chem. Nov.-Dec. 1998;9(6):635-44.

Cunningham et al., "Cetuximab monotherapy and cetuximab plus irinotecan in irinotecan-refractory metastatic colorectal cancer", N Engl J Med. Jul. 22, 2004;351(4):337-45.

Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.

Edelman et al., "The covalent structure of an entire gammaG immunoglobulin molecule", Proc Natl Aced Sci U S A. May 1969;63(1):78-85.

Feldmann et al., "Design of effective immunotherapy for human autoimmunity", Nature. Jun. 2, 2005;435(7042):612-9.

Fukuda et al., "Evaluation of novel platinum complexes, inhibitors of topoisomerase I and II in non-small cell lung cancer (NSCLC) sublines resistant to cisplatin", Anticancer Res. Mar.-Apr. 1995;15(2):393-8.

Garcia-Giron et al., "Phase II trial of fortnightly irinotecan (CPT-11) in the treatment of colorectal cancer patients resistant to previous fluoropyrimidine-based chemotherapy", Clin Transl Oncol. Jul. 2005;7(6):244-9.

Goldenberg et al., "Selective in vivo therapeutic efficacies of SN-38 conjugates of an anti-CEACAM5 antibody in preclinical models of human colon carcinoma", Presentation, ASCO 2009 Gastrointestinal Cancers Symposium, San Francisco, CA, Jan. 15-17, 2009.

Goldenberg, D.M., "Challenging the Dogmas: Clinical Efficacy of SN-38-Conjugated Antibodies in Solid Tumors", 26th EORTC-NCI-AACR Symposium on Molecular Targets and Cancer Therapeutics, Barcelona, Spain, Nov. 18-21, 2014.

Goldenberg, D.M., "SN-38 Conjugates for Therapy of Advanced Solid Cancers", 5th Annual World ADC Summit in San Diego, CA, Oct. 26-29, 2014.

Goldenberg et al., "Therapy of human solid tumor xenografts with CD74-targeted milatuzumab-SN-38 immunoconjugates", Poster, 2012 ASCO Annual Meeting, Chicago, IL, Jun. 1-5, 2012.

Goldenberg et al., "Improved Therapeutic Index of IMMU-132 ADC vs. Irinotecan in Preclinical Studies", Presentation, AACR Annual Meeting, San Diego, CA, Apr. 5-9, 2014.

Gomez-Manzano et al., "Delta-24 increases the expression and activity of topoisomerase I and enhances the antiglioma effect of irinotecan", Clin Cancer Res. Jan. 15, 2006;12(2):556-62.

Gorman, G. "Focused on Therapy: Cancer, Autoimmune & Other Serious Diseases", Presentation, Oppenheimer 23rd Annual Healthcare Conference, NYC, Dec. 12, 2012.

Govindan et al., "Targeted therapy of human colonic, lung, and pancreatic cancer xenografts, growing in nude mice, with potent antibody conjugates of SN-38", Poster, AACR 100th Annual Meeting, Denver, CO, Apr. 18-22, 2009.

Govindan et al., "Efficacious therapies of two human pancreatic cancer xenografts and an aggressive human lymphoma xenograft with redesigned antibody-SN-38 conjugates", Poster, AACR 101st Annual Meeting, Washington, DC, Apr. 17-21, 2010.

Govindan et al., "Optimal cleavable linker for antibody-SN-38 conjugates for cancer therapy: Impact of linker's stability on efficacy", Poster, AACR 103rd Annual Meeting, Chicago, IL, Mar. 31-Apr. 4, 2012.

Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.

Govindan et al., "New antibody conjugates in cancer therapy", ScientificWorldJournal. Oct. 12, 2010;10:2070-89.

Govindan et al., "CEACAM5-targeted therapy of human colonic and pancreatic cancer xenografts with potent abetuzumab-SN-38 immunoconjugates", Clin Cancer Res. Oct. 1, 2009;15(19):6052-61.

Govindan et al., "Improving the Therapeutic Index in Cancer Therapy by Using Antibody-Drug Conjugates Designed with a Moderately Cytotoxic Drug", Mol Pharm. Nov. 25, 2014. [Epub ahead of print].

Govindan et al., "Milatuzumab-SN-38 conjugates for the treatment of CD74+ cancers", Mol Cancer Ther. Jun. 2013;12(6):968-78.

Guarino et al., "Therapy of advanced metastatic lung cancer with an anti-Trop-2-SN-38 antibody-drug conjugate (ADC), sacituzumab govitecan (IMMU-132): Phase I/II clinical experience", J Clin Oncol 33, 2015 (suppl; abstr 2504), Retrieved from http://meetinglibrary.asco.org/content/148373-156.

Gura, T., "Systems for identifying new drugs are often faulty", Science. Nov. 7, 1997;278(5340):1041-2.

(56) References Cited

OTHER PUBLICATIONS

He et al., "Synthesis and biological evaluation of bis and monocarbonate prodrugs of 10-hydroxycamptothecins", Bioorg Med Chem. Aug. 1, 2004;12(15):4003-8.
Horwitz et al., "Antiviral action of camptothecin", Antimicrob Agents Chemother. Nov. 1972;2(5):395-401.
Kaiser, J., "Cancer. First pass at cancer genome reveals complex landscape", Science. Sep. 8, 2006;313(5792):1370.
Karacay et al., "Combining antibody-targeted radiation (radioimmunotherapy) and antibody-SN-38 conjugates (ADC) improves pancreatic cancer therapy", Poster, AACR 101st Annual Meeting, Washington, DC, Apr. 17-21, 2010.
Kufe et al., Non-Intercalating Topoisomerase-Targeting Drugs, Holland-Frei Cancer Medicine, Hamilton (ON), BC Decker (2003).
Kufe et al., Topoisomerase Biology, 6th Ed., Holland-Frei Cancer Medicine, Hamilton (ON), BC Decker (2003).
Mahato et al., "Prodrugs for improving tumor targetability and efficiency", Adv Drug Deliv Rev. Jul. 18, 2011;63(8):659-70.
Matsumura et al., "Preclinical and clinical studies of NK012, an SN-38-incorporating polymeric micelles, which is designed based on EPR effect", Adv Drug Deliv Rev. Mar. 18, 2011;63(3):184-92.
Mine Safety and Health Administration (Special Hazards of Acetylene, Sep. 16, 2011).
Moon et al., "Cross-linker evaluation in the design of antibody-SN-38 conjugates for cancer therapy", Poster, AACR 101st Annual Meeting, Washington, DC, Apr. 17-21, 2010.
Segal et al., "IMMU-130, an SN-38 antibody-drug conjugate (ADC) targeting CEACAM5, is therapeutically active in metastatic colorectal cancer (mCRC): Initial clinical results of two Phase I studies", Presentation, AACR Annual Meeting, San Diego, CA, Apr. 5-9, 2014.
Sharkey et al., "Epratuzumab-SN-38: a new antibody-drug conjugate for the therapy of hematologic malignancies", Mol Cancer Ther. Jan. 2012;11(1):224-34.
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Stanford University Environmental Health and Safety (Information on Azide Compounds, Dec. 2, 2008).
Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].
Starodub et al., "Phase I/II trial of IMMU-132 (isactuzumab govitecan), an anti-Trop-2-SN-38 antibody drug conjugate (ADC): Results in patients with metastatic gastrointestinal (GI) cancers", J Clin Oncol 33, 2015 (suppl 3; abstr 703), Retrieved from http://meetinglibrary.asco.org/content/140198-158.
Starodub et al., "IMMU-132, an SN-38 antibody-drug conjugate (ADC) targeting Trop-2, as a novel platform for the therapy of diverse metastatic solid cancers: Clinical results", Poster, the 2014 Annual Meeting of the American Society of Clinical Oncology (ASCO), May 30-Jun. 3, 2014.
Talmadge et al., "Murine models to evaluate novel and conventional therapeutic strategies for cancer", Am J Pathol. Mar. 2007;170(3):793-804.
Thurber et al., "Antibody tumor penetration: transport opposed by systemic and antigen-mediated clearance", Adv Drug Deliv Rev. Sep. 2008;60(12):1421-34.
Van Noort and Amor, "Cell Biology of Autoimmune Disease", vol. 178, pp. 127-206; International Rev. of Cytology, 1998.
Dang et al., "Hypoxia-inducible factor-1 target genes as indicators of tumor vessel response to vascular endothelial growth factor inhibition", Cancer Res. Mar. 15, 2008;68(6):1872-80.
Declaration under 37 C.F.R. 1.132 by David M. Goldenberg, filed in U.S. Appl. No. 13/948,732 dated Jun. 20, 2014.
Declaration under 37 C.F.R. 1.132 by David M. Goldenberg, filed in U.S. Appl. No. 14/204,698 dated Jan. 7, 2015.
Jefferis et al., "Human immunoglobulin allotypes: possible implications for immunogenicity", MAbs. Jul.-Aug. 2009;1(4):332-8.
LiquidBiopsy Platform for automated rare cell isolation, Specification Sheet, 2015 Thermo Fisher Scientific Inc.
NCT01270698 (Jan. 3, 2011, pp. 1-4).
NCT01605318 (May 22, 2012, pp. 1-4).
Reagan-Shaw et al., "Dose translation from animal to human studies revisited", FASEB J. Mar. 2008;22(3):659-61.
Segal et al., "IMMU-130, an Sn-38 antibody-drug conjugate (ADC) targeting CEACAM5, is therapeutically active in metastatic colorectal cancer (mCRC): Initial clinical results of two Phase I studies", 2014 AACR Meeting Apr. 5-9, 2-14, San Diego, CA (Abstract No. CT211).
Seruga et al., "Failures in Phase III: Causes and Consequences", Clin Cancer Res. Oct. 15, 2015;21(20):4552-60.

\* cited by examiner

SEQUENCE LISTING

```
<160> NUMBER OF SEQ ID NOS: 96

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Lys Ala Ser Gln Asp Val Ser Ile Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Tyr Arg Tyr Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln His Tyr Ile Thr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Tyr Gly Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Thr Tyr Thr Gly Glu Pro Thr Tyr Thr Asp Asp Phe Lys
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Phe Gly Ser Ser Tyr Trp Tyr Phe Asp Val
1               5                   10

<210> SEQ ID NO 7
<211> LENGTH: 330
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 7

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide -continued

```
<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser His Ile Gln Ile Pro Pro Gly Leu Thr Glu Leu Leu Gln Gly Tyr
1               5                   10                  15
```

```
Thr Val Glu Val Leu Arg Gln Gln Pro Pro Asp Leu Val Glu Phe Ala
         20                  25                  30

Val Glu Tyr Phe Thr Arg Leu Arg Glu Ala Arg Ala
         35                  40

<210> SEQ ID NO 10
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
                20                  25                  30

Ala Val Glu Tyr Phe Thr Arg Leu Arg Glu Ala Arg Ala
            35                  40                  45

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Ile Glu Tyr Leu Ala Lys Gln Ile Val Asp Asn Ala Ile Gln Gln
1               5                   10                  15

Ala

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 13
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
                20                  25                  30

Pro Met Ala Phe Leu Arg Glu Tyr Phe Glu Arg Leu Glu Lys Glu Glu
            35                  40                  45
```

Ala Lys
    50

<210> SEQ ID NO 14
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 16
<211> LENGTH: 51
<212> TYPE: PRT
<213> ORGANISM: Homo sapiens

<400> SEQUENCE: 16

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 17
<211> LENGTH: 54
<212> TYPE: PRT
<213> ORGANISM: Homo sapiens

<400> SEQUENCE: 17

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 18
<211> LENGTH: 44
<212> TYPE: PRT
<213> ORGANISM: Homo sapiens

<400> SEQUENCE: 18

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 19
<211> LENGTH: 44
<212> TYPE: PRT
<213> ORGANISM: Homo sapiens

<400> SEQUENCE: 19

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

```
<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40
```

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 32
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 33
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala

```
                35                  40

<210> SEQ ID NO 34
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 35
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 36
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 37
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30
```

Val Glu Tyr Phe Thr Arg Leu Arg Glu Ala Arg Ala
            35                  40

<210> SEQ ID NO 38
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
            35                  40

<210> SEQ ID NO 39
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
            35                  40

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Ile Glu Tyr Leu Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Leu Glu Tyr Leu Ala Lys Gln Ile Val Asp Asn Ala Ile Gln Gln
1               5                   10                  15

Ala

<210> SEQ ID NO 42
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 42

Gln Val Glu Tyr Leu Ala Lys Gln Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Asp Tyr Leu Ala Lys Gln Ile Val Asp Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Phe Leu Ala Lys Gln Ile Val Asp Asn Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Thr Leu Ala Lys Gln Ile Val Asp Asn Ala Ile Gln Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Ser Leu Ala Lys Gln Ile Val Asp Asn Ala Ile Gln Gln
1               5                   10                  15

Ala

<210> SEQ ID NO 47
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Ile Ala Lys Gln Ile Val Asp Asn Ala Ile Gln Gln
1               5                   10                  15

Ala

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Val Ala Lys Gln Ile Val Asp Asn Ala Ile Gln Gln
1               5                   10                  15

Ala

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Arg Gln Ile Val Asp Asn Ala Ile Gln Gln
1               5                   10                  15

Ala

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Leu Ala Lys Asn Ile Val Asp Asn Ala Ile Gln Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Leu Ala Lys Gln Ile Val Glu Asn Ala Ile Gln Gln
1               5                   10                  15

Ala

<210> SEQ ID NO 52
```

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr Leu Ala Lys Gln Ile Val Asp Gln Ala Ile Gln Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Leu Ala Lys Gln Ile Val Asp Asn Ala Ile Asn Gln
1               5                   10                  15

Ala

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Ile Glu Tyr Leu Ala Lys Gln Ile Val Asp Asn Ala Ile Gln Asn
1               5                   10                  15

Ala

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Ile Glu Tyr Leu Ala Lys Gln Ile Val Asp Asn Ala Ile Gln Gln
1               5                   10                  15

Leu

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ile Glu Tyr Leu Ala Lys Gln Ile Val Asp Asn Ala Ile Gln Gln
1               5                   10                  15

Ile

```
<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ile Glu Tyr Leu Ala Lys Gln Ile Val Asp Asn Ala Ile Gln Gln
1               5                   10                  15

Val

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ile Glu Tyr Val Ala Lys Gln Ile Val Asp Tyr Ala Ile His Gln
1               5                   10                  15

Ala

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Ile Glu Tyr Lys Ala Lys Gln Ile Val Asp His Ala Ile His Gln
1               5                   10                  15

Ala

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Ile Glu Tyr His Ala Lys Gln Ile Val Asp His Ala Ile His Gln
1               5                   10                  15

Ala

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ile Glu Tyr Val Ala Lys Gln Ile Val Asp His Ala Ile His Gln
1               5                   10                  15

Ala
```

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Leu Glu Tyr Gln Ala Gly Leu Leu Val Gln Asn Ala Ile Gln Gln
1               5                   10                  15

Ala Ile

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Leu Ile Glu Thr Ala Ser Ser Leu Val Lys Asn Ala Ile Gln Leu
1               5                   10                  15

Ser Ile

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Ile Glu Glu Ala Ala Ser Arg Ile Val Asp Ala Val Ile Glu Gln
1               5                   10                  15

Val Lys

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Leu Tyr Gln Phe Ala Asp Arg Phe Ser Glu Leu Val Ile Ser Glu
1               5                   10                  15

Ala Leu

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Glu Gln Val Ala Asn Gln Leu Ala Asp Gln Ile Ile Lys Glu Ala
1               5                   10                  15

Thr

```
<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Glu Glu Leu Ala Trp Lys Ile Ala Lys Met Ile Trp Ser Asp Val
1               5                   10                  15

Phe

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Leu Val Arg Leu Ser Lys Arg Leu Val Glu Asn Ala Val Leu Lys
1               5                   10                  15

Ala Val

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Ala Glu Glu Val Ser Ala Arg Ile Val Gln Val Val Thr Ala Glu
1               5                   10                  15

Ala Val

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ile Lys Gln Ala Ala Phe Gln Leu Ile Ser Gln Val Ile Leu Glu
1               5                   10                  15

Ala Thr

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Ala Trp Lys Ile Ala Lys Met Ile Val Ser Asp Val Met Gln Gln
1               5                   10                  15
```

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Glu Gln Tyr Ala Asn Gln Leu Ala Asp Gln Ile Ile Lys Glu Ala
1               5                   10                  15

Thr Glu

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Glu Glu Leu Ala Trp Lys Ile Ala Lys Met Ile Trp Ser Asp Val
1               5                   10                  15

Phe Gln Gln Cys
            20

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Ile Glu Tyr Leu Ala Lys Gln Ile Pro Asp Asn Ala Ile Gln Gln
1               5                   10                  15

Ala

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Gly Ala Asp Leu Ile Glu Glu Ala Ala Ser Arg Ile Val Asp Ala
1               5                   10                  15

```
Val Ile Glu Gln Val Lys Ala Ala Gly
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 81

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 85
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 86
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Leu Glu Lys Gln Tyr Gln Glu Gln Leu Glu Glu Glu Val Ala Lys Val
1               5                   10                  15

Ile Val Ser Met Ser Ile Ala Phe Ala
            20                  25

<210> SEQ ID NO 88
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 89
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Asn Gly Ile Leu Glu Leu Glu Thr Lys Ser Ser Lys Leu Val Gln Asn

```
                1               5                   10                  15
Ile Ile Gln Thr Ala Val Asp Gln Phe
                20                  25

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Gln Asp Lys Asn Tyr Glu Asp Glu Leu Thr Gln Val Ala Leu Ala
1               5                   10                  15

Leu Val Glu Asp Val Ile Asn Tyr Ala
                20                  25

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Thr Ser Ala Lys Asp Asn Ile Asn Ile Glu Glu Ala Ala Arg Phe
1               5                   10                  15

Leu Val Glu Lys Ile Leu Val Asn His
                20                  25

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Phe Pro Lys Pro Ser Thr Pro Pro Gly Ser Ser Gly Gly Ala Pro
1               5                   10                  15

<210> SEQ ID NO 94
<211> LENGTH: 44
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
```

```
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Asn or Gln
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 94

Xaa Xaa Ile Xaa Ile Pro Pro Xaa Leu Xaa Xaa Leu Leu Xaa Xaa Tyr
1               5                   10                  15
```

```
Xaa Val Xaa Val Leu Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40
```

```
<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 95

Xaa Xaa Xaa Xaa Xaa Ala Xaa Xaa Ile Val Xaa Xaa Ala Ile Xaa Xaa
1               5                   10                  15

Xaa

<210> SEQ ID NO 96
<211> LENGTH: 44
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(1)
<223> OTHER INFORMATION: Ser or Thr
```

```
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 96

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
            35                  40
```

ISOLATION, DETECTION, DIAGNOSIS AND/OR CHARACTERIZATION OF CIRCULATING TROP-2-POSITIVE CANCER CELLS

RELATED APPLICATIONS

This application claims the benefit under 35 U.S.C. 119(e) of U.S. Provisional Patent Application 62/151,169, filed Apr. 22, 2015, the text of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 21, 2016, is named IMM359US1_SL.txt and is 44,983 bytes in size.

BACKGROUND OF THE INVENTION

Field of the Invention

This invention relates to methods and compositions for isolating, detecting, diagnosing and/or characterizing Trop-2+ cancer cells, preferably from the circulation. The methods and compositions utilize anti-Trop-2 antibodies, which may be monovalent, bivalent or multivalent. In a preferred embodiment, anti-Trop-2 antibodies are the sole anti-TAA (tumor-associated antigen) capture antibodies utilized in the assay, which does not include use of mixtures of antibodies against TAAs other than Trop-2. In alternative embodiments, the capture antibody may be a bispecific antibody comprising an anti-Trop-2 antibody or fragment and a second antibody or fragment against a different TAA. More preferably, the antibodies are rodent, chimeric, humanized or human antibodies or antigen-binding fragments thereof. Expression of Trop-2 in cancer cells may be assessed using known techniques, including but not limited to binding of anti-Trop-2 antibodies as detected by flow cytometry or immunohistochemistry, and quantitative RT-PCR. Automated systems and devices that have been developed to isolate and/or detect circulating tumor cells (CTCs), including but not limited to the MagSweeper device (Illumina, Inc., San Diego, Calif.), LIQUIDBIOPSY® system (Cynvenio Biosystems, Inc., Westlake Village, Calif.), CELLSEARCH® system (Vendex LLC, Raritan, N.J.), GILUPI CELLCOLLECTOR™ (GILUPI GmbH, Potsdam, Germany), APOSTREAM® system (Apocell, Houston, Tex.), ONCOCEE™ microfluidic platform (BioCept Laboratories, San Diego, Calif.), VerIFAST System (Casavant et al., 2013, Lab Chip 13:391-6; 2014, Lab Chip 14:99-105) or ISOFLUX™ system (Fluxion, South San Francisco, Calif.) may be utilized in the practice of the claimed methods. Most preferably, the anti-Trop-2 antibody is a murine, chimeric or humanized RS7 (hRS7) antibody, comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6). However, in alternative embodiments other known anti-Trop-2 antibodies may be utilized, as discussed below. The methods and compositions are applicable for the enrichment, isolation, detection, diagnosis and/or characterization of various metastatic Trop-2-expressing cancers, such as breast (e.g., triple-negative breast cancer), ovarian, cervical, endometrial, lung, prostate, colon, rectum, stomach, esophageal, bladder, renal, pancreatic, thyroid, epithelial, and head-and-neck cancers. Anti-Trop-2 antibodies may be utilized in combination with one or more labeled detection antibodies, or may be directly labeled by conjugation with at least one diagnostic agent. Alternatively, a bispecific antibody may comprise one binding site for Trop-2 and another binding site for a hapten on a targetable construct, typically a small peptide labeled with at least one diagnostic agent. In certain alternative embodiments, detection of Trop-2+ CTCs may be followed by therapeutic treatment of the Trop-2+ cancer, using anti-Trop-2 antibodies or fragments thereof. Preferably the antibody or fragment is conjugated to at least one therapeutic agent, such as antibodies, antibody fragments, drugs, toxins, nucleases, hormones, immunomodulators, pro-apoptotic agents, anti-angiogenic agents, boron compounds, photoactive agents or dyes or radioisotopes. More preferably, the therapeutic agent is SN-38 or P2PDOX.

Related Art

Trop-2 (human trophoblast-cell-surface marker) is a cell surface glycoprotein that was originally identified in normal and malignant trophoblast cells (Lipinski et al., 1981, Proc Natl. Acad Sci USA 78:5147-50). Trop-2 is highly expressed in most human carcinomas, particularly in epithelial carcinomas and adenocarcinomas, with reported low to restricted expression in normal tissues (see, e.g., Cubas et al., 2010, Molec Cancer 9:253; Stepan et al., 2011, J Histochem Cytochem 59:701-10; Varughese et al., 2011, Am J Obst Gyn 205:567e-e7). Expression of Trop-2 is associated with metastasis, increased tumor aggressiveness and decreased patient survival (Cubas et al., 2010; Varughese et al., 2011). Pathogenic effects of Trop-2 have been reported to be mediated, at least in part, by the ERK ½MAPK pathway (Cubas et al., 2010).

It has been proposed that early in tumor progression, cancer cells may be found in low concentration in the circulation (see, e.g., Krishnamurthy et al., 2013, Cancer Medicine 2:226-33; Alix-Panabieres & Pantel, 2013, Clin Chem 50:110-18; Wang et al., Feb. 24, 2015, Int J Clin Oncol, Epub ahead of print). Due to the relatively non-invasive nature of blood sample collection, there has been great interest in the isolation and detection of CTCs, to promote cancer diagnosis at an earlier stage of the disease and as a predictor for tumor progression, disease prognosis and/or responsiveness to drug therapy (see, e.g., Alix-Panabieres & Pantel, 2013, Clin Chem 50:110-18; Winer-Jones et al., 2014, PLoS One 9:e86717; U.S. Patent Appl. Publ. No. 2014/0357659).

Various techniques and apparatus have been developed to isolate and/or detect circulating tumor cells. Several reviews of the field have recently been published (see, e.g., Alix-Panabieres & Pantel, 2013, Clin Chem 50:110-18; Joosse et al., 2014, EMBO Mol Med 7:1-11; Truini et al., 2014, Fron Oncol 4:242). The techniques have involved enrichment and/or isolation of CTCs, generally using capture antibodies against an antigen expressed on tumor cells, and separation with magnetic nanoparticles, microfluidic devices, filtration, magnetic separation, centrifugation, flow cytometry and/or cell sorting devices (e.g., Krishnamurthy et al., 2013, Cancer Medicine 2:226-33; Alix-Panabieres & Pantel, 2013, Clin Chem 50:110-18; Joosse et al., 2014, EMBO Mol Med 7:1-11; Truini et al., 2014, Fron Oncol 4:242; Powell et al., 2012, PLoS ONE 7:e33788; Winer-Jones et al., 2014, PLoS One 9:e86717; Gupta et al., 2012, Biomicrofluidics 6:24133; Saucedo-Zeni et al., 2012, Int J Oncol 41:1241-50; Harb et al., 2013, Transl Oncol 6:528-38). The enriched or isolated CTCs may then be analyzed using a variety of known methods, as discussed further below. Systems or apparatus that have been used for CTC isolation and detection include the CELLSEARCH® system (e.g., Truini et al., 2014, Front Oncol 4:242), MagSweeper device (e.g., Powell et al., 2012, PLoS ONE 7:e33788), LIQUIDBIOPSY® system (Winer-Jones et al., 2014, PLoS One 9:e86717), APOSTREAM® system (e.g., Gupta et al., 2012, Biomicrofluidics 6:24133), GILUPI CELLCOLLECTOR™ (e.g., Saucedo-Zeni et al., 2012, Int J Oncol 41:1241-50), and ISOFLUX™ system (Harb et al., 2013, Transl Oncol 6:528-38).

To date, the only FDA-approved technology for CTC detection involves the CELLSEARCH® platform (Vendex LLC, Raritan, N.J.), which utilizes anti-EpCAM antibodies attached to magnetic nanoparticles to capture CTCs. Detection of bound cells occurs with fluorescent-labeled antibodies against cytokeratin (CK) and CD45. Fluorescently labeled cells bound to magnetic particles are separated out using a strong magnetic field and are counted by digital fluorescence microscopy. The CELLSEARCH® system has received FDA approval for detection of metastatic breast, prostate and colorectal cancers.

Most CTC detection systems have focused on use of anti-EpCAM capture antibodies (see, e.g., Truini et al., 2014, Front Oncol 4:242; Powell et al., 2012, PLoS ONE 7:e33788; Alix-Panabieres & Pantel, 2013, Clin Chem 50:110-18; Lin et al., 2013, Biosens Bioelectron 40:63-67; Wang et al., Feb. 24, 2015, Int J Clin Oncol Epub ahead of print; Magbanua et al., 2015, Clin Cancer Res 21:1098-105; Harb et al., 2013, Transl Oncol 6:528-38). However, not all metastatic tumors express EpCAM (see, e.g., Mikolajcyzyk et al., 2011, J Oncol 2011:252361; Pecot et al., 2011, Cancer Discovery 1:580-86; Gupta et al., 2012, Biomicrofluidics 6:24133). Attempts have been made to utilize alternative schemes for isolating and detecting EpCAM-negative CTCs, such as use of antibody combinations against TAAs. Antibodies against as many as 10 different TAAs have been utilized in an attempt to increase recovery of metastatic circulating tumor cells (e.g., Mikolajcyzyk et al., 2011, J Oncol 2011:252361; Pecot et al., 2011, Cancer Discovery 1:580-86; Krishnamurthy et al., 2013, Cancer Medicine 2:226-33; Winer-Jones et al., 2014, PLoS One 9:e86717).

Drawbacks exist to such approaches, including the complexity of preparing and using large numbers of different antibodies and their attachment to magnetic nanoparticles, microfluidic devices or other separation technologies, as well as potential cross-reactivity against normal cell populations when using a broad spectrum of anti-tumor antibodies. A need exists in the art for improved methods of isolating, detecting, diagnosing and/or characterizing CTCs, using antibodies against a single TAA that is expressed in a broad range of tumors.

SUMMARY

In various embodiments, the present invention concerns enrichment, isolation, detection, diagnosis and/or characterization of Trop-2-positive circulating tumor cells (CTCs) using anti-Trop-2 antibodies and/or antigen-binding fragments thereof. The anti-Trop-2 antibody may be used to enrich and/or isolate tumor cells from the circulation. Bound CTCs may be detected by a variety of known techniques and/or apparatus, as discussed in detail below. Any known method for detecting biomarkers of isolated CTCs may be utilized, such as FISH, FACS, fluorescence microscopy, fluorescent detection, flow cytometry, immunohistochemistry, microchip-based systems, RT-PCR, ELISA, or any other technique known in the art for detecting the presence of cancer cells.

In a specific embodiment, the anti-Trop-2 antibody may be a murine, chimeric or humanized RS7 antibody (see, e.g., U.S. Pat. No. 7,238,785, the Figures and Examples section of which are incorporated herein by reference), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6). However, as discussed below other anti-Trop-2 antibodies are known and may be used.

The anti-Trop-2 antibody moiety may be a monoclonal antibody, an antigen-binding antibody fragment, a bispecific or multivalent antibody, or other antibody-based molecule. The antibody can be of various isotypes, preferably human IgG1, IgG2, IgG3 or IgG4, more preferably comprising human IgG1 hinge and constant region sequences. The antibody or fragment thereof can be a rodent, chimeric, a humanized, or a human antibody, as well as variations thereof, such as half-IgG4 antibodies (referred to as "unibodies"), as described by van der Neut Kolfschoten et al. (*Science* 2007; 317:1554-1557). More preferably, the antibody or fragment thereof may be designed or selected to comprise human constant region sequences that belong to specific allotypes, such as G1m3, G1m3,1, G1m3,2 or G1m3,1,2. More preferably, the allotype is selected from the group consisting of the nG1m1, G1m3, nG1 m1,2 and Km3 allotypes.

Where bispecific antibodies are used to capture CTCs, the antibody may comprises at least one anti-Trop-2 antibody or fragment thereof, and at least one antibody or fragment thereof against a different TAA. Exemplary TAAs may include carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1-α, AFP, PSMA, CEACAM5, CEACAM-6, c-met, B7, ED-B of fibronectin, Factor H, FHL-1, Flt-3, folate receptor, GROB, HMGB-1, hypoxia inducible factor (HIF), insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5ac, NCA-95, NCA-90, Ia, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, or C5. Preferably, the TAA is selected from the group consisting of CEACAM5, MUC5ac, CD74, HLA-DR, CSAp, AFP (alpha-fetoprotein), HER2, vimentin, EGFR, IGF-1R, PD-L1 and PD-L2.

Because the detected tumors will be Trop-2-positive, they may be treated with anti-Trop-2 antibodies, such as anti-Trop-2 antibody-drug conjugates (ADCs). An anti-Trop-2 antibody may initially be used to detect and/or quantify expression or gene copy number of Trop-2 in the CTC. Such analysis may be used to predict response to therapeutic anti-Trop-2 antibodies, as well as to monitor response of the tumor(s) to treatment. As discussed below, immunoconjugates of anti-Trop-2 antibodies may include any known therapeutic agent, such as a chemotherapeutic agent. A number of cytotoxic drugs of use for cancer treatment are well-known in the art and any such known drug may be conjugated to the antibody of interest. In a preferred embodiment, the drug conjugated to the antibody is a camptothecin or anthracycline, most preferably SN-38 or a pro-drug form of 2-pyrrolinodoxorubicin (2-PDox) (see, e.g., U.S. Pat. Nos. 8,877,202 and 8,750,496, the Figures and Examples section of each incorporated herein by reference). The drug to be conjugated to the anti-Trop-2 antibody or antibody fragment may be selected from the group consisting of an anthracycline, a camptothecin, a tubulin inhibitor, a maytansinoid, a calicheamycin, an auristatin, a nitrogen mustard, an ethylenimine derivative, an alkyl sulfonate, a nitrosourea, a triazene, a folic acid analog, a taxane, a COX-2 inhibitor, a pyrimidine analog, a purine analog, an antibiotic, an enzyme inhibitor, an epipodophyllotoxin, a platinum coordination complex, a vinca alkaloid, a substituted urea, a methyl hydrazine derivative, an adrenocortical suppressant, a hormone antagonist, an antimetabolite, an alkylating agent, an antimitotic, an anti-angiogenic agent, a tyrosine kinase inhibitor, an mTOR inhibitor, a heat shock protein (HSP90) inhibitor, a proteosome inhibitor, an HDAC inhibitor, a pro-apoptotic agent, and a combination thereof.

The anti-Trop-2 antibodies are of use for detection, diagnosis, characterization and/or treatment of Trop-2 expressing cancers, such as breast, ovarian, cervical, endometrial, lung, prostate, colon, rectum, stomach, esophageal, bladder, renal, pancreatic, thyroid, epithelial or head-and-neck cancers. The methods and compositions may be of particular use for detection and/or treatment of metastatic colorectal cancer, triple-negative breast cancer, HER+, ER+, progesterone+breast cancer, metastatic non-small-cell lung cancer (NSCLC), metastatic small-cell lung cancer (SCLC), metastatic pancreatic cancer, metastatic renal cell carcinoma, metastatic gastric cancer, metastatic esophageal cancer, metastatic urothelial cancer, or metastatic prostate cancer.

DETAILED DESCRIPTION

Definitions

Unless otherwise specified, "a" or "an" means one or more.

As used herein, "about" means plus or minus 10%. For example, "about 100" would include any number between 90 and 110.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')₂, Fab', Fab, Fv, sFv and the like. Antibody fragments may also include single domain antibodies and IgG4 half-molecules, as discussed below. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins").

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

A human antibody is, e.g., an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous murine heavy chain and light chain loci. The transgenic mice can synthesize human antibodies specific for particular antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, the Examples section of which are incorporated herein by reference.

A "diagnostic agent" is an atom, molecule, or compound that is useful in diagnosing a disease. Useful diagnostic agents include, but are not limited to, radioisotopes, dyes, contrast agents, luminescent agents, chemiluminescent agents, fluorescent compounds or molecules and enhancing agents (e.g., paramagnetic ions). Preferably, the diagnostic agents are selected from the group consisting of radioisotopes, enhancing agents, and fluorescent compounds.

A therapeutic agent is a compound, molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. Therapeutic agents of use are described in more detail below.

An immunoconjugate is an antibody, antibody fragment or fusion protein conjugated to at least one therapeutic and/or diagnostic agent.

A multispecific antibody is an antibody that can bind simultaneously to at least two targets that are of different structure, e.g., two different antigens, two different epitopes on the same antigen, or a hapten and/or an antigen or epitope. Multispecific, multivalent antibodies are constructs that have more than one binding site, and the binding sites are of different specificity.

A bispecific antibody is an antibody that can bind simultaneously to two different targets. Bispecific antibodies (bsAb) and bispecific antibody fragments (bsFab) may have at least one arm that specifically binds to, for example, a tumor-associated antigen and at least one other arm that specifically binds to a targetable conjugate that bears a therapeutic or diagnostic agent. A variety of bispecific fusion proteins can be produced using molecular engineering.

FIGURE LEGENDS

FIG. 1. Analysis of Trop-2 copy number by FISH. MCF-7 (Trop-2 positive) cells were analyzed by FISH. Trop-2 copy number was determined using anti-Trop-2 and anti-chromosome-1 specific probes (Empire Genomics, Buffalo, N.Y.).

Figure 2:
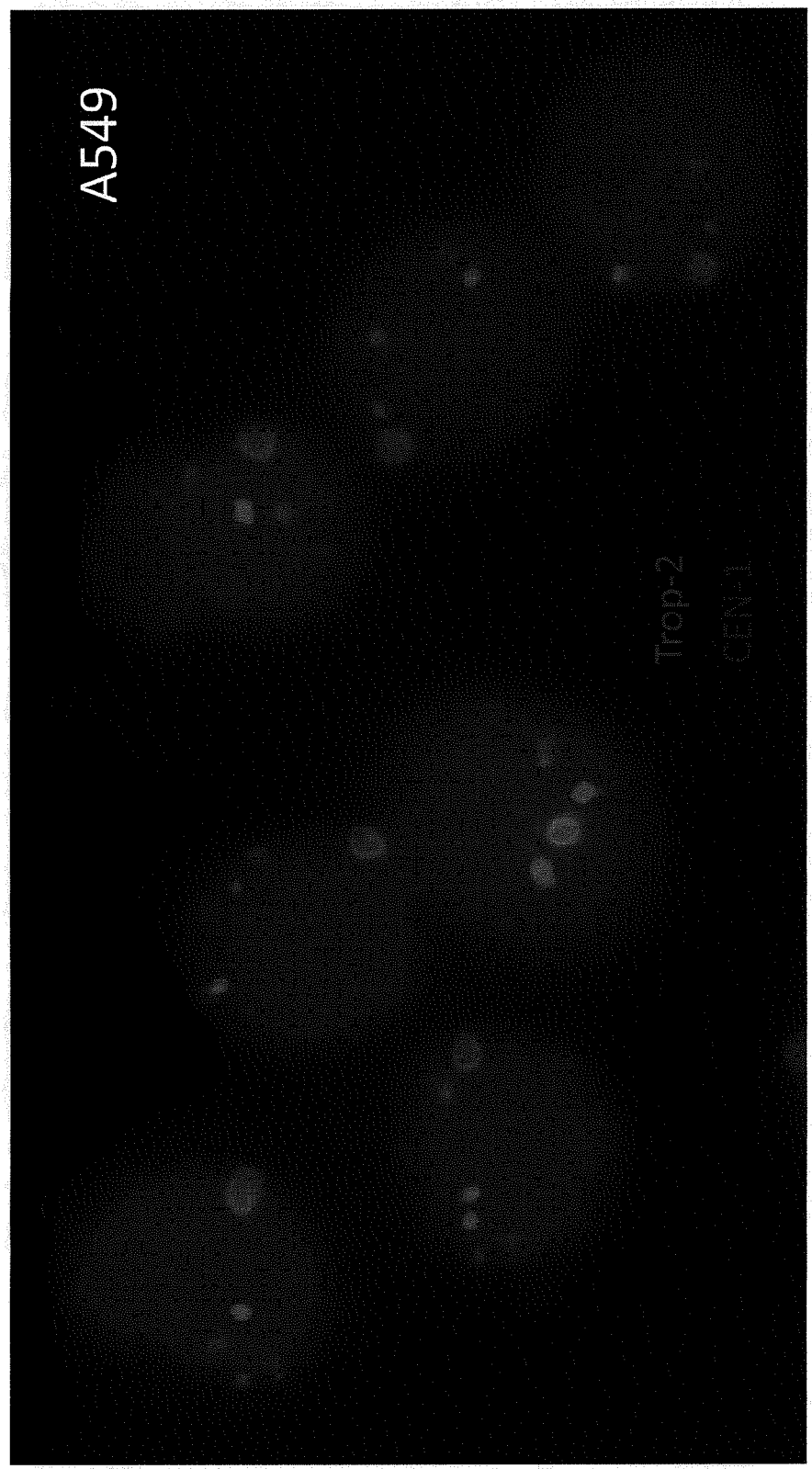

FIG. 2. Analysis of Trop-2 copy number by FISH. A549 (Trop-2 negative) cells were analyzed by FISH. Trop-2 copy number was determined using anti-Trop-2 and anti-chromosome-1 specific probes (Empire Genomics, Buffalo, N.Y.).

Figure 3:
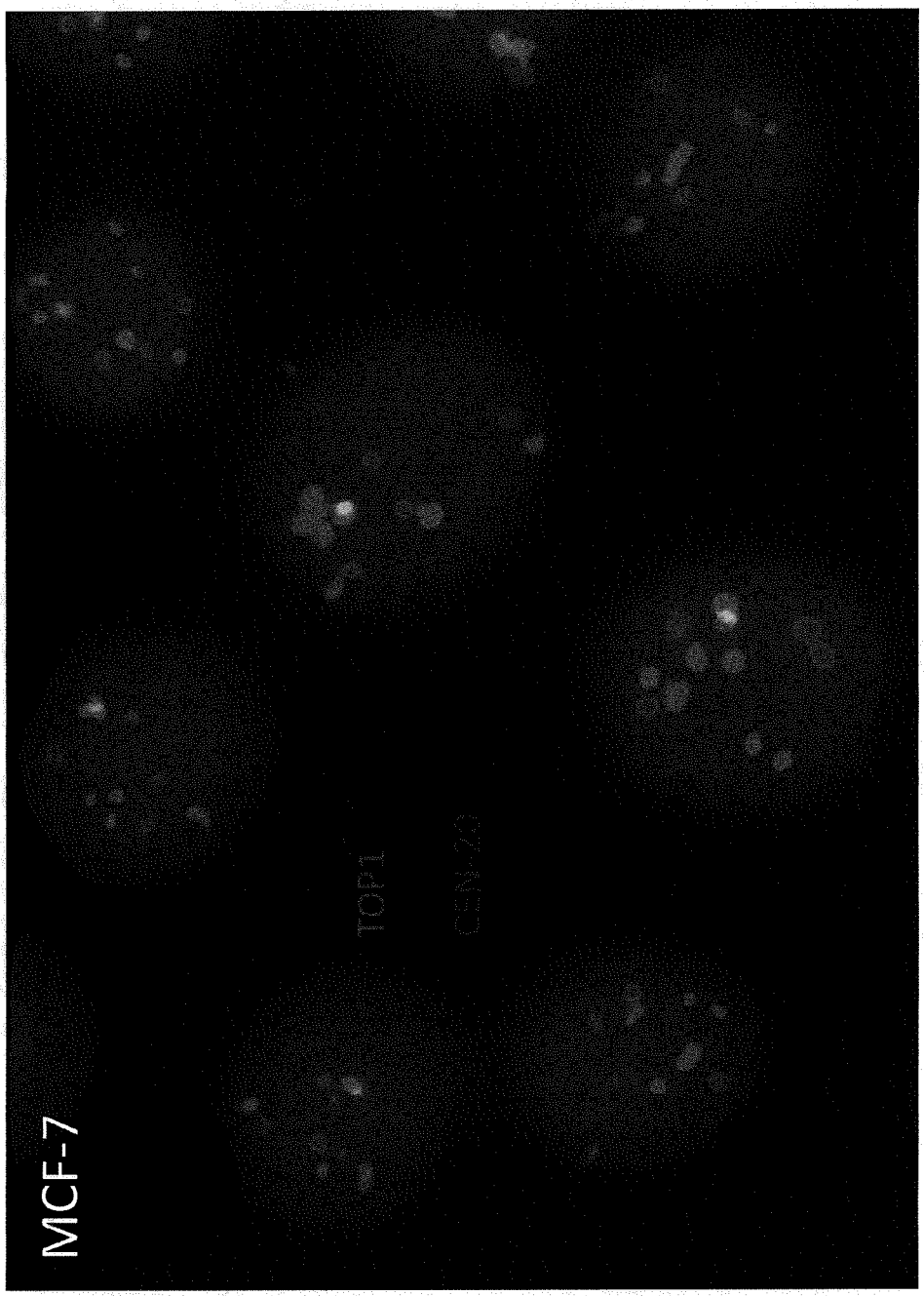

FIG. 3. Analysis of topoisomerase-I copy number by FISH. MCF-7 cells were analyzed by FISH. Topoisomerase I (TOP1) copy number was determined using anti-TOP1 and anti-chromosome-20 specific probes (ABNOVA®, Taipei, Taiwan).

Figure 4:
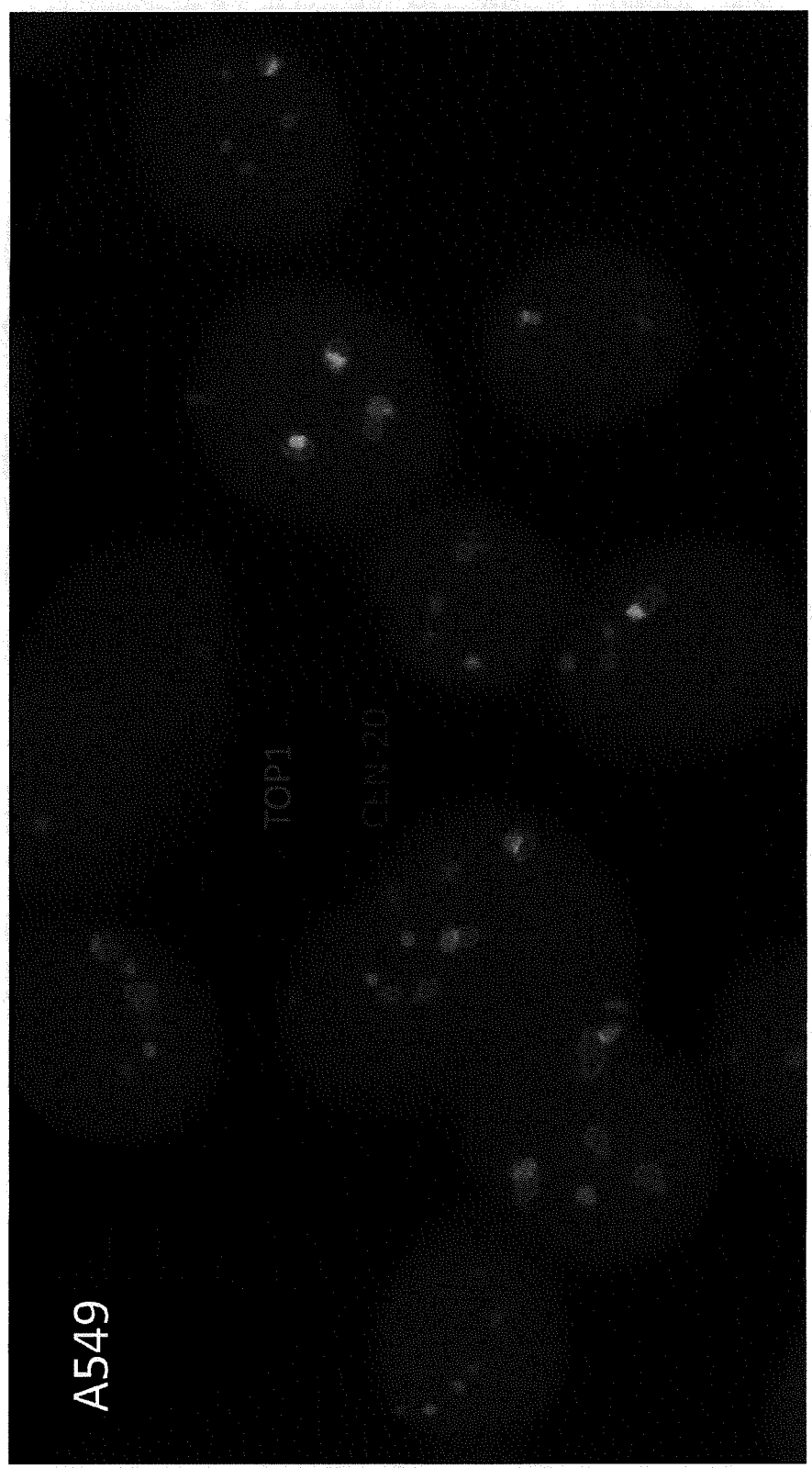

FIG. 4. Analysis of topoisomerase-I copy number by FISH. A549 cells were analyzed by FISH. Topoisomerase I (TOP1) copy number was determined using anti-TOP1 and anti-chromosome-20 specific probes (ABNOVA®, Taipei, Taiwan).

ANTI-TROP-2 ANTIBODIES

The subject methods and compositions for CTC isolation and/or detection utilize at least one antibody or fragment thereof that binds to Trop-2, including rodent, chimeric, human or humanized antibodies. In a specific preferred embodiment, the anti-Trop-2 antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGF-GSSYWYFDV, SEQ ID NO:6).

The RS7 antibody was a murine $IgG_1$ raised against a crude membrane preparation of a human primary squamous cell lung carcinoma. (Stein et al., Cancer Res. 50: 1330, 1990) The RS7 antibody recognizes a 46-48 kDa glycoprotein, characterized as cluster 13. (Stein et al., Int. J. Cancer Supp. 8:98-102, 1994) The antigen was designated as EGP-1 (epithelial glycoprotein-1), but is also referred to as Trop-2.

Trop-2 is a type-I transmembrane protein and has been cloned from both human (Fornaro et al., Int J Cancer 1995; 62:610-8) and mouse cells (Sewedy et al., Int J Cancer 1998; 75:324-30). In addition to its role as a tumor-associated calcium signal transducer (Ripani et al., Int J Cancer 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5). Trop-2 is highly expressed in the vast majority of human tumors and animal models of cancer (McDougall et al., 2015, Dev Dyn 244:99-109).

The utility of Trop-2 as a marker for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell (Fong et al., Modern Pathol 2008; 21:186-91) carcinomas. The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

Flow cytometry and immunohistochemical staining studies have shown that the RS7 MAb detects antigen on a variety of tumor types, with limited binding to normal human tissue (Stein et al., 1990). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., 1990; Stein et al., 1991). Drug-conjugated RS7 MAb in animal models also have shown targeting and therapeutic efficacy of human cancer xenografts (Cardillo et al., Clinical Cancer Res., 17:3157-69, 2011).

Strong RS7 staining has been demonstrated in tumors from the lung, breast, bladder, ovary, uterus, stomach, and prostate. (Stein et al., Int. J. Cancer 55:938, 1993) The lung cancer cases comprised both squamous cell carcinomas and adenocarcinomas. (Stein et al., Int. J. Cancer 55:938, 1993) Both cell types stained strongly, indicating that the RS7 antibody does not distinguish between histologic classes of non-small-cell carcinoma of the lung.

While the hRS7 antibody is preferred, other anti-Trop-2 antibodies are known and/or publicly available and in alternative embodiments may be utilized in the subject methods and compositions. While humanized or human antibodies are preferred for reduced immunogenicity, in alternative embodiments a chimeric antibody may be of use, while rodent MAbs can be useful for in-vitro and ex-vivo studies. As discussed below, methods of antibody humanization are well known in the art and may be utilized to convert an available murine or chimeric antibody into a humanized form.

Anti-Trop-2 antibodies are commercially available from a number of sources and include LS-C126418, LS-C178765, LS-C126416, LS-C126417 (LifeSpan BioSciences, Inc., Seattle, Wash.); 10428-MM01, 10428-MM02, 10428-R001, 10428-R030 (Sino Biological Inc., Beijing, China); MR54 (eBioscience, San Diego, Calif.); sc-376181, sc-376746, Santa Cruz Biotechnology (Santa Cruz, Calif.); MM0588-

49D6, (Novus Biologicals, Littleton, Colo.); ab79976, and ab89928 (ABCAM®, Cambridge, Mass.).

Other anti-Trop-2 antibodies have been disclosed in the patent literature. For example, U.S. Publ. No. 2013/0089872 discloses anti-Trop-2 antibodies K5-70 (Accession No. FERM BP-11251), K5-107 (Accession No. FERM BP-11252), K5-116-2-1 (Accession No. FERM BP-11253), T6-16 (Accession No. FERM BP-11346), and T5-86 (Accession No. FERM BP-11254), deposited with the International Patent Organism Depositary, Tsukuba, Japan. U.S. Pat. No. 5,840,854 disclosed the anti-Trop-2 monoclonal antibody BR110 (ATCC No. HB11698). U.S. Pat. No. 7,420,040 disclosed an anti-Trop-2 antibody produced by hybridoma cell line AR47A6.4.2, deposited with the IDAC (International Depository Authority of Canada, Winnipeg, Canada) as accession number 141205-05. U.S. Pat. No. 7,420,041 disclosed an anti-Trop-2 antibody produced by hybridoma cell line AR52A301.5, deposited with the IDAC as accession number 141205-03. U.S. Publ. No. 2013/0122020 disclosed anti-Trop-2 antibodies 3E9, 6G11, 7E6, 15E2, 18B1. Hybridomas encoding a representative antibody were deposited with the American Type Culture Collection (ATCC), Accession Nos. PTA-12871 and PTA-12872. U.S. Pat. No. 8,715,662 discloses anti-Trop-2 antibodies produced by hybridomas deposited at the AID-ICLC (Genoa, Italy) with deposit numbers PD 08019, PD 08020 and PD 08021. U.S. Patent Application Publ. No. 20120237518 discloses anti-Trop-2 antibodies 77220, KM4097 and KM4590. U.S. Pat. No. 8,309,094 (Wyeth) discloses antibodies A1 and A3, identified by sequence listing. The Examples section of each patent or patent application cited above in this paragraph is incorporated herein by reference. For non-patent publications, Lipinski et al. (1981, Proc Natl. Acad Sci USA, 78:5147-50) disclosed anti-Trop-2 antibodies 162-25.3 and 162-46.2. More recently, the Pr1E11 anti-Trop-2 antibody was reported to recognize a unique epitope on Trop-2 (Ikeda et al., Biochem Biophys Res Comm 458:877-82).

Numerous anti-Trop-2 antibodies are known in the art and/or publicly available. As discussed below, methods for preparing antibodies against known antigens were routine in the art. The sequence of the human Trop-2 protein was also known in the art (see, e.g., GenBank Accession No. CAA54801.1). Methods for producing humanized, human or chimeric antibodies were also known. The person of ordinary skill, reading the instant disclosure in light of general knowledge in the art, would have been able to make and use the genus of anti-Trop-2 antibodies.

None of the prior studies discussed above contained any disclosure of the use of anti-Trop-2 antibodies for isolating or detecting Trop-2 positive CTCs. A need exists for compositions and methods for enriching, isolating, detecting, diagnosing and/or characterizing Trop-2 positive CTCs.

Isolation and Detection of Circulating Tumor Cells

The anti-Trop-2 antibodies may be utilized to enrich, isolate, detect and/or diagnose Trop-2 positive CTCs using any known technology for CTC isolation and detection. Numerous systems have been developed and are commercially available for CTC detection. Although the majority were developed using specific anti-EpCAM antibodies, the compositions and methods may be modified to utilize anti-Trop-2 antibodies instead. Thus, isolation and detection of Trop-2 positive CTCs may be performed using any such known system, or more traditional methods of cell isolation and detection. Non-limiting examples of such known techniques are discussed below.

The present invention may be used with an affinity-based enrichment step, as well as methods without an enrichment steps, such as MAINTRAC® (Pachmann et al. 2005, Breast Cancer Res, 7: R975). Methods that use a magnetic device for affinity-based enrichment, include the CELLSEARCH® system (Veridex), the LIQUIDBIOPSY® platform (Cynvenio Biosystems) and the MagSweeper device (Talasaz et al, PNAS, 2009, 106: 3970). Methods that do not use a magnetic device for affinity-based enrichment, include a variety of fabricated microfluidic devices, such as CTC-chips (Stott et al. 2010, Sci Transl Med, 2: 25ra23), HB-chips (Stott et al, 2010, PNAS, 107: 18392), NanoVelcro chips (Lu et al., 2013, Methods, 64: 144), GEDI microdevice (Kirby et al., 2012, PLoS ONE, 7: e35976), and Biocept's ONCOCEE™ technology (Pecot et al., 2011, Cancer Discov, 1: 580).

Use of the FDA-approved CELLSEARCH® system for CTC detection in non-small cell and small cell lung cancer patients is discussed in Truini et al. (2014, Front Oncol 4:242). A 7.5 ml sample of peripheral blood is mixed with magnetic iron nanoparticles coated with an nanti-EpCAM antibody. A strong magnetic field is used to separate EpCAM positive from EpCAM-negative cells. Detection of bound CTCs was performed using fluorescently labeled anti-CK and anti-CD45 antibodies, along with DAPI (4',6'diamidino-2-phynlindole) fluorescent labeling of cell nuclei. CTCs were identified by fluorescent detection as CK positive, CD45 negative and DAPI positive.

The VerIFAST system was used for diagnosis and pharmacodynamic analysis of circulating tumor cells (CTCs) in non-small cell lung cancer (NSCLC) (Casavant et al., 2013, Lab Chip 13:391-6; 2014, Lab Chip 14:99-105). The VerIFAST platform utilizes the relative dominance of surface tension over gravity in the microscale to load immiscible phases side by side. This pins aqueous and oil fields in adjacent chambers to create a virtual filter between two aqueous wells (Casavant et al., 2013, Lab Chip 13:391-6). Using paramagnetic particles (PMPs) with attached antibody or other targeting moieties, specific cell populations can be targeted and isolated from complex backgrounds through a simple traverse of the oil barrier. In the NSCLC example, streptavidin was conjugated to DYNABEADS® FLOWCOMP™ PMPs (Life Technologies, USA) and cells were captured using biotinylated anti-EpCAM antibody. A handheld magnet was used to transfer CTCs bound to PMPs between aqueous chambers. Collected CTCs were released with PMP release buffer (DYNABEADS®) and stained for EpCAM, EGFR or transcription termination factor (TTF-1).

The VerIFAST platform integrates a microporous membrane into an aqueous chamber to enable multiple fluid transfers without the need for cell transfer or centrifugation. With physical characteristic scales enabling high precision relative to macroscale techniques, such microfluidic techniques are well adapted to capture and assess CTCs with minimal sample loss. The VerIFAST platform effectively captured CTCs from blood of NSCLC patients.

The GILUPI CELLCOLLECTOR™ (Saucedo-Zeni et al., 2012, Int J Oncol 41:1241-50) is based on a functionalized medical Seldinger guidewire (FSMW) coated with chimeric anti-EpCAM antibody. The guidewire was functionalized with a polycarboxylate hydrogel layer that was activated with EDC and NHS, allowing covalent bonding of antibody. The antibody-coated FSMW was inserted in the cubital veins of breast cancer or NSCLC lung cancer patients through a standard venous cannula for 30 minutes. Following binding of cells to the guidewire, CTCs were identified by immunocytochemical staining of EpCAM and/ or cytokeratins and nuclear staining. Fluorescent labeling was analyzed with an Axio Imager.A1m microscope (Zeiss, Jena, Germany) equipped with an AxioCam digital camera system and AxioVision 4.6 software. The FSMW system was capable of enriching EpCAM-positive CTCs from 22 of 24 patients tested, including those with early stage cancer in which distant metasteses had not yet been diagnosed. No CTCs were detected in healthy volunteers. An advantage of the FSMW system is that it is not limited by the volume of ex vivo blood samples that may be processed using alternative methodologies, such as the CELLSEARCH® system. Estimated blood volume in contact with the FSMW during the 30 minute exposure was 1.5 to 3 liters.

The MagSweeper device (e.g., Powell et al., 2012, PLoS ONE 7:e33788) is another system utilized antibody-coated magnetic particles for CTC detection. Nine milliliters of whole blood was mixed ex vivo for 1 hr at RT with 4.5 μM DYNABEADS® (Invitrogen, Life Technologies, Grand Island, N.Y.) coated with the BerEP4 anti-EpCAM antibody. After dilution with PBS, cells bound to DYNABEADS® were captured by a sweeping magnetic device (MagSweeper, see FIG. 1 of Powel et al., 2012). Two cycles of capture-wash-relase were performed, using a controlled shear force that released non-specifically bound leukocytes and RBCs. Captured cells were released into fresh buffer and examined using an Axio Observer A1 inverted microscope (Zeiss). Single CTCs were manually aspirated and stored frozen, prior to analysis of expression of 87 genes by chip based high-throughput qRT-PCR.

Gupta et al. (2012, Biomicrofluidics 6:24133) discussed use of the APOSTREAM™ dielectrophoretic device for CTC collection and analysis. A microfluidic flow chamber is used with dielectrophoretic (DEP) technology to capture CTCs (see FIG. 1, Gupta et al., 2012). The system may be operated in continuous mode for flow-through isolation and enrichment of CTCs from peripheral blood. DEP sorts cells with distinct biophysical characteristics by exploiting the frequency-dependent dielectric properties of different cell types, arising from differences in morphologic properties and electrical conductivity. These differences result in differential frequency-dependent migration of CTCs and normal cells in the microfluidic chamber. At an AC frequency in the range of 45-85 kHz, cancer cells experience a positive (attractive) DEP force, which causes them to migrate towards the electrode plane and away from the hydrodynamic flow through the chamber. At the same frequency, normal cells experience a negative (repulsive) DEP force, which moves them into the hydrodynamic flow velocity profile and out of the chamber. A collection port is used to remove separated CTCs for further analysis. For the initial optimization study, cultured cancer cells were spiked into normal blood mononuclear cells and were recovered with over a 70% efficiency. Although the APOSTREAM™ system disclosed by Gupta does not use capture antibodies, the subject anti-Trop-2 antibodies may potentially be utilized to increase the efficiency of CTC separation and/or for post-separation characterization of the isolated CTCs.

Winer-Jones et al. (2014, PLoS One 9:e86717) discussed use of the LIQUIDBIOPSY® system for isolation and characterization of CTCs. The LIQUIDBIOPSY® system uses high throughput sheath flow microfluidics through a flow cell, combined with anti-EpCAM antibodies as a capture agent. Biotinylated anti-EpCAM was attached to streptavidin-coated IMAG™ beads (BD, Franklin Lakes, N.J.) and mixed with blood samples, containing spiked tumor cells labeled with CFSE or FITC. Normal nucleated cells were labeled with DAPI. After antibody binding, the blood samples were processed on the CTC flow cell, attached to a glass slide. An external magnetic field is used to capture magnetic-bead bound CTCs on the glass surface, separating them from the laminar flow containing normal cells. Captured cells were counted using an Eclipse E80i fluorescent microscope (Nikon Instruments, Melville, N.Y.).

The person of ordinary skill will realize that any of these systems, or any other known system for CTC enrichment and/or isolation, may be used with the subject anti-Trop-2 antibodies for enrichment, isolation, detection and/or characterization of CTCs. Where an anti-Trop-2 capture antibody is utilized, the bound CTCs may be detected and/or characterized using labeled antibodies against a different Trop-2 epitope, or against other known tumor-associated antigens, including but not limited to carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1-α, AFP, PSMA, CEACAM5, CEACAM-6, c-met, B7, ED-B of fibronectin, Factor H, FHL-1, Flt-3, folate receptor, GROB, HMGB-1, hypoxia inducible factor (HIF), insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5ac, NCA-95, NCA-90, Ia, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, and C5.

Antibody Preparation

Techniques for preparing monoclonal antibodies against virtually any target antigen, such as Trop-2, are well known in the art. See, for example, Köhler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs)

of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 6: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50). A fully human antibody also can be constructed by genetic or chromosomal transfection methods, as well as phage display technology, all of which are known in the art. See for example, McCafferty et al., *Nature* 348:552-553 (1990). Where antibodies are to be utilized in vivo, for example in tumor therapy following detection of a Trop-2 positive cancer, such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Known Antibodies and Target Antigens

As discussed above, in certain alternative embodiments the anti-Trop-2 antibodies are of use for treating Trop-2-expressing cancers, following detection of circulating Trop-2-positive tumor cells. In some embodiments, the target cancer may express one or more additional tumor-associated antigens (TAAs) that may be targeted for tumor therapy.

Particular antibodies that may be of use for therapy of cancer include, but are not limited to, LL1 (anti-CD74), LL2 or RFB4 (anti-CD22), veltuzumab (hA20, anti-CD20), rituximab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as Trop-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMIVIU-31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Alternative antibodies of use include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), muromonab-CD3 (anti-CD3 receptor), natalizumab (anti-α4 integrin), omalizumab (anti-IgE); anti-TNF-α antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), and Benlysta (Human Genome Sciences).

Other useful tumor-associated antigens that may be targeted include carbonic anhydrase IX, B7, CCL19, CCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD47, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., AVASTIN®, fibronectin splice variant), ED-B fibronectin (e.g., L19), EGP-1 (Trop-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-β, HMGB-1, hypoxia inducible factor (HIF), HM1.24, HER-2/neu, histone H2B, histone H3, histone H4, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (P1GF), PSA (prostate-specific antigen), PSMA, PAM4 antigen, PD-1 receptor, PD-L1, NCA-95, NCA-90, A3, A33, Ep-CAM, KS-1, Le(y), mesothelin, 5100, tenascin, TAC, Tn antigen, Thomas-Friedenreich antigens, tumor necrosis antigens, tumor angiogenesis antigens, TNF-α, TRAIL receptor (R1 and R2), Trop-2, VEGFR, RANTES, T101, as well as cancer stem cell antigens, complement factors C3, C3a, C3b, C5a, C5, and an oncogene product.

Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3): 385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8). Another useful target for breast cancer therapy is the LIV-1 antigen described by Taylor et al. (*Biochem. J.* 2003; 375: 51-9).

Checkpoint-inhibitor antibodies have been used in cancer therapy. Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response against tumor tissues. Exemplary checkpoint inhibitor antibodies against cytotoxic T-lymphocyte antigen 4 (CTLA4, also known as CD152), programmed cell death protein 1 (PD1, also known as CD279), programmed cell death 1 ligand 1 (PD-L1, also known as CD274) and programmed cell death 1 ligand 2 (PD-L2) (Latchman et al., 2001, Nat Immunol 2:261-8), may be used in combination with one or more other agents to enhance the effectiveness of immune response against disease cells, tissues or pathogens. Exemplary anti-PD1 antibodies include lambrolizumab (MK-3475, MERCK), nivolumab (BMS-936558, BRISTOL-MYERS SQUIBB), AMP-224 (MERCK), and pidilizumab (CT- 011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4). Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1). Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, J Transl Med 11:89).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, and colon (e.g., Meyer-Siegler et al., 2004, *BMC Cancer* 12:34; Shachar & Haran, 2011, *Leuk Lymphoma* 52:1446-54). Milatuzumab (hLL1) is an exemplary anti-CD74 antibody of therapeutic use for treatment of MIF-mediated diseases.

Various other antibodies of use are known in the art (e.g., U.S. Pat. Nos. 5,686,072; 5,874,540; 6,107,090; 6,183,744; 6,306,393; 6,653,104; 6,730,300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.)

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including tumor-associated antigens, have been deposited at the ATCC and/or have published variable region sequences and are available for use in the claimed methods and compositions. See, e.g., U.S. Pat. Nos. 7,312,318; 7,282, 567; 7,151,164; 7,074,403; 7,060,802; 7,056,509; 7,049, 060; 7,045,132; 7,041,803; 7,041,802; 7,041,293; 7,038, 018; 7,037,498; 7,012,133; 7,001,598; 6,998,468; 6,994, 976; 6,994,852; 6,989,241; 6,974,863; 6,965,018; 6,964, 854; 6,962,981; 6,962,813; 6,956,107; 6,951,924; 6,949, 244; 6,946,129; 6,943,020; 6,939,547; 6,921,645; 6,921, 645; 6,921,533; 6,919,433; 6,919,078; 6,916,475; 6,905, 681; 6,899,879; 6,893,625; 6,887,468; 6,887,466; 6,884, 594; 6,881,405; 6,878,812; 6,875,580; 6,872,568; 6,867, 006; 6,864,062; 6,861,511; 6,861,227; 6,861,226; 6,838, 282; 6,835,549; 6,835,370; 6,824,780; 6,824,778; 6,812, 206; 6,793,924; 6,783,758; 6,770,450; 6,767,711; 6,764, 688; 6,764,681; 6,764,679; 6,743,898; 6,733,981; 6,730, 307; 6,720,155; 6,716,966; 6,709,653; 6,693,176; 6,692, 908; 6,689,607; 6,689,362; 6,689,355; 6,682,737; 6,682, 736; 6,682,734; 6,673,344; 6,653,104; 6,652,852; 6,635, 482; 6,630,144; 6,610,833; 6,610,294; 6,605,441; 6,605, 279; 6,596,852; 6,592,868; 6,576,745; 6,572,856; 6,566, 076; 6,562,618; 6,545,130; 6,544,749; 6,534,058; 6,528, 625; 6,528,269; 6,521,227; 6,518,404; 6,511,665; 6,491, 915; 6,488,930; 6,482,598; 6,482,408; 6,479,247; 6,468, 531; 6,468,529; 6,465,173; 6,461,823; 6,458,356; 6,455, 044; 6,455,040; 6,451,310; 6,444,206; 6,441,143; 6,432, 404; 6,432,402; 6,419,928; 6,413,726; 6,406,694; 6,403, 770; 6,403,091; 6,395,276; 6,395,274; 6,387,350; 6,383, 759; 6,383,484; 6,376,654; 6,372,215; 6,359,126; 6,355, 481; 6,355,444; 6,355,245; 6,355,244; 6,346,246; 6,344, 198; 6,340,571; 6,340,459; 6,331,175; 6,306,393; 6,254, 868; 6,187,287; 6,183,744; 6,129,914; 6,120,767; 6,096, 289; 6,077,499; 5,922,302; 5,874,540; 5,814,440; 5,798, 229; 5,789,554; 5,776,456; 5,736,119; 5,716,595; 5,677, 136; 5,587,459; 5,443,953; 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Stickler et al., 2011). It has been reported that G1m1 antibodies contain allotypic sequences that tend to induce an immune response when administered to non-G1m1 (nG1m1) recipients, such as G1m3 patients (Stickler et al., 2011). Non-G1m1 allotype antibodies are not as immunogenic when administered to G1m1 patients (Stickler et al., 2011).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown below for the exemplary antibodies rituximab (SEQ ID NO:7) and veltuzumab (SEQ ID NO:8).

```
Rituximab heavy chain variable region sequence
                                       (SEQ ID NO: 7)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLFPPKPKDTLMISRTPEVTCVVVDVS
```

-continued

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Veltuzumab heavy chain variable region
(SEQ ID NO: 8)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | |
|---|---|---|---|---|---|
| | Complete allotype | 214 (allotype) | 356/358 (allotype) | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Nanobodies

Nanobodies are single-domain antibodies of about 12-15 kDa in size (about 110 amino acids in length). Nanobodies can selectively bind to target antigens, like full-size antibodies, and have similar affinities for antigens. However, because of their much smaller size, they may be capable of better penetration into solid tumors. The smaller size also contributes to the stability of the nanobody, which is more resistant to pH and temperature extremes than full size antibodies (Van Der Linden et al., 1999, Biochim Biophys Act 1431:37-46). Single-domain antibodies were originally developed following the discovery that camelids (camels, alpacas, llamas) possess fully functional antibodies without light chains (e.g., Hamsen et al., 2007, Appl Microbiol Biotechnol 77:13-22). The heavy-chain antibodies consist of a single variable domain ($V_{HH}$) and two constant domains ($C_H2$ and $C_H3$). Like antibodies, nanobodies may be developed and used as multivalent and/or bispecific constructs. Humanized forms of nanobodies are in commercial development that are targeted to a variety of target antigens, such as IL-6R, vWF, TNF, RSV, RANKL, IL-17A & F and IgE (e.g., ABLYNX®, Ghent, Belgium), with potential clinical use in cancer and other disorders (e.g., Saerens et al., 2008, Curr Opin Pharmacol 8:600-8; Muyldermans, 2013, Ann Rev Biochem 82:775-97; Ibanez et al., 2011, J Infect Dis 203:1063-72).

The plasma half-life of nanobodies is shorter than that of full-size antibodies, with elimination primarily by the renal route. Because they lack an Fc region, they do not exhibit complement dependent cytotoxicity.

Nanobodies may be produced by immunization of camels, llamas, alpacas or sharks with target antigen, following by isolation of mRNA, cloning into libraries and screening for antigen binding. Nanobody sequences may be humanized by standard techniques (e.g., Jones et al., 1986, Nature 321: 522, Riechmann et al., 1988, Nature 332: 323, Verhoeyen et al., 1988, Science 239: 1534, Carter et al., 1992, Proc. Nat'l Acad. Sci. USA 89: 4285, Sandhu, 1992, Crit. Rev. Biotech. 12: 437, Singer et al., 1993, J. Immun. 150: 2844). Humanization is relatively straight-forward because of the high homology between camelid and human FR sequences.

In various embodiments, the subject antibodies may comprise nanobodies for targeted delivery of conjugated diagnostic agent(s) to targeted cancer cells. Nanobodies of use are disclosed, for example, in U.S. Pat. Nos. 7,807,162; 7,939,277; 8,188,223; 8,217,140; 8,372,398; 8,557,965; 8,623,361 and 8,629,244, the Examples section of each incorporated herein by reference.)

Antibody Fragments

Antibody fragments are antigen binding portions of an antibody, such as F(ab')$_2$, Fab', F(ab)$_2$, Fab, Fv, sFv, scFv and the like. Antibody fragments which recognize specific epitopes can be generated by known techniques. F(ab')$_2$ fragments, for example, can be produced by pepsin digestion of the antibody molecule. These and other methods are described, for example, by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9: 132-137 (1991).

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007).

An antibody fragment can also be prepared by proteolytic hydrolysis of a full-length antibody or by expression in E. coli or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 kD fragment denoted F(ab')$_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

General Techniques for Antibody Cloning and Production

Various techniques, such as production of chimeric or humanized antibodies, may involve procedures of antibody cloning and construction. The antigen-binding Vκ (variable light chain) and V$_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned V$_L$ and V$_H$ genes can be expressed in cell culture as a chimeric Ab as described by Orlandi et al., (Proc. Natl. Acad. Sci., USA, 86: 3833 (1989)). Based on the V gene sequences, a humanized MAb can then be designed and constructed as described by Leung et al. (Mol. Immunol., 32: 1413 (1995)).

cDNA can be prepared from any known hybridoma line or transfected cell line producing a murine MAb by general molecular cloning techniques (Sambrook et al., Molecular Cloning, A laboratory manual, 2$^{nd}$ Ed (1989)). The Vκ sequence for the MAb may be amplified using the primers VK1BACK and VK1FOR (Orlandi et al., 1989) or the extended primer set described by Leung et al. (BioTechniques, 15: 286 (1993)). The V$_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (Mol. Immunol., 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for V$_H$ can be subcloned into a similar staging vector, such as the pBluescript-based VHpBS. Expression cassettes containing the Vκ and V$_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human MAb. Alternatively, the V$_κ$ and V$_H$ expression cassettes can be excised and subcloned into a single expression vector, such as pdHL2, as described by Gillies et al. (J. Immunol. Methods 125:191 (1989) and also shown in Losman et al., Cancer, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Bispecific and Multispecific Antibodies

In certain alternative embodiments, the anti-Trop-2 antibody or fragment thereof may be co-administered with, for example, a hapten-binding antibody or fragment thereof, such as an anti-HSG or anti-In-DTPA antibody. Such bispecific antibodies may be of use in pretargeting techniques for administration of diagnostic and/or therapeutic agents to Trop-2 positive tumors in vivo. In other embodiments, bispecific or multispecific antibodies may be utilized directly for anti-cancer therapy.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv), as discussed above. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "DOCK-AND-LOCK®" (DNL®), discussed in more detail below, has been utilized to produce combinations of virtually any desired antibodies, antibody fragments and other effector molecules. Any of the techniques known in the art for making bispecific or multispecific antibodies may be utilized in the practice of the presently claimed methods.

DOCK-AND-LOCK® (DNL®)

Bispecific or multispecific antibodies or other constructs may be produced using the DOCK-AND-LOCK® technology (see, e.g., U.S. Pat. Nos. 7,550,143; 7,521,056; 7,534,866; 7,527,787 and 7,666,400, the Examples section of each incorporated herein by reference). Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell Biol. 2004; 5: 959). The DDD and AD peptides may be attached to any protein, peptide or other molecule, preferably as a fusion protein comprising the AD or DDD sequence. Because the DDD sequences spontaneously dimerize and bind to the AD sequence, the technique allows the formation of complexes between any selected molecules that may be attached to DDD or AD sequences.

Although the standard DNL® complex comprises a trimer with two DDD-linked molecules attached to one AD-linked molecule, variations in complex structure allow the formation of dimers, trimers, tetramers, pentamers, hexamers and other multimers. In some embodiments, the DNL® complex may comprise two or more antibodies, antibody fragments or fusion proteins which bind to the same antigenic determinant or to two or more different antigens. The DNL® complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues of RIIα (Newlon et al., Nat. Struct. Biol. 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL® complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL® constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described below, virtually any protein or peptide may be incorporated into a DNL® construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL® constructs, different AD or DDD sequences may be utilized. Exemplary DDD and AD sequences are provided below.

```
DDD1
                                    (SEQ ID NO: 9)
SHIQIPPGLTELLQGYTVEVLRQQPPDLVEFAVEYFTRLREARA

DDD2
                                    (SEQ ID NO: 10)
CGHIQIPPGLTELLQGYTVEVLRQQPPDLVEFAVEYFTRLREARA

AD1
                                    (SEQ ID NO: 11)
QIEYLAKQIVDNAIQQA

AD2
                                    (SEQ ID NO: 12)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                    (SEQ ID NO: 13)
SLRECELYVQKHNIQALLKDSIVQLCTARPERPMAFLREYFERLEKEEAK

DDD3C
                                    (SEQ ID NO: 14)
MSCGGSLRECELYVQKHNIQALLKDSIVQLCTARPERPMAFLREYFERL
EKEEAK

AD3
                                    (SEQ ID NO: 15)
CGFEELAWKIAKMIWSDVFQQGC
```

In other alternative embodiments, other sequence variants of AD and/or DDD moieties may be utilized in construction of the DNL® complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα

(SEQ ID NO: 16)
SLRECELYVQKHNIQALLKDVSIVQLCTARPERPMAFLREYFEKLEKEEAK

PKA RIβ

(SEQ ID NO: 17)
SLKGCELYVQLHGIQQVLKDCIVHLCISKPERPMKFLREHFEKLEKEENRQILA

PKA RIIα

(SEQ ID NO: 18)
SHIQIPPGLTELLQGYTVEVGQQPPDLVDFAVEYFTRLREARRQ

PKA RIIβ

(SEQ ID NO: 19)
SIEIPAGLTELLQGFTVEVLRHQPADLLEFALQHFTRLQQENER of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:20 to SEQ ID NO:39 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 2

Conservative Amino Acid Substitutions in DDD1 (SEQ ID NO: 9). Consensus sequence disclosed as SEQ ID NO: 94.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K |   | N |   |   |   | A |   | S | D |   |   | N | A |   | S |   | D |   |   | K |
|   | R |   |   |   |   |   |   |   |   |   |   |   |   |   |   |   |   |   |   |   |   |
| Q | Q | P | P | D | L | V | E | F | A | V | E | Y | F | T | R | L | R | E | A | R | A |
| N | N |   |   |   | E |   | D |   | L | I | D |   |   | S | K |   | K | D | L | K | L |
|   |   |   |   |   |   |   |   |   |   | V |   |   |   |   |   |   |   |   | I |   | I |
|   |   |   |   |   |   |   |   |   |   |   |   |   |   |   |   |   |   |   | V |   | V |

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:9 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

(SEQ ID NO: 9)
SH<u>IQ</u>IPPG<u>L</u>TE<u>LL</u>QG<u>Y</u>T<u>V</u>E<u>V</u>LRQQPPD<u>LVEFAVEYF</u>TR<u>L</u>REARA

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:9 are shown in Table 2. In devising Table 2, only highly conservative amino acid substitutions were considered. For example, charged residues were only substituted for residues (SEQ ID NO: 20)
THIQIPPGLTELLQGYTVEVLRQQPPDLVEFAVEYFTRLREARA (SEQ ID NO: 21)
SKIQIPPGLTELLQGYTVEVLRQQPPDLVEFAVEYFTRLREARA (SEQ ID NO: 22)
SRIQIPPGLTELLQGYTVEVLRQQPPDLVEFAVEYFTRLREARA (SEQ ID NO: 23)
SHINIPPGLTELLQGYTVEVLRQQPPDLVEFAVEYFTRLREARA (SEQ ID NO: 24)
SHIQIPPALTELLQGYTVEVLRQQPPDLVEFAVEYFTRLREARA (SEQ ID NO: 25)
SHIQIPPGLSELLQGYTVEVLRQQPPDLVEFAVEYFTRLREARA (SEQ ID NO: 26)
SHIQIPPGLTDLLQGYTVEVLRQQPPDLVEFAVEYFTRLREARA (SEQ ID NO: 27)
SHIQIPPGLTELLNGYTVEVLRQQPPDLVEFAVEYFTRLREARA (SEQ ID NO: 28)
SHIQIPPGLTELLQAYTVEVLRQQPPDLVEFAVEYFTRLREARA (SEQ ID NO: 29)
SHIQIPPGLTELLQGYSVEVLRQQPPDLVEFAVEYFTRLREARA (SEQ ID NO: 30)
SHIQIPPGLTELLQGYTVDVLRQQPPDLVEFAVEYFTRLREARA (SEQ ID NO: 31)
SHIQIPPGLTELLQGYTVEVLKQQPPDLVEFAVEYFTRLREARA (SEQ ID NO: 32)
SHIQIPPGLTELLQGYTVEVLRNQPPDLVEFAVEYFTRLREARA

```
                                              (SEQ ID NO: 33)
SHIQIPPGLTELLQGYTVEVLRQNPPDLVEFAVEYFTRLREARA (SEQ ID NO: 34)
SHIQIPPGLTELLQGYTVEVLRQQPPELVEFAVEYFTRLREARA (SEQ ID NO: 35)
SHIQIPPGLTELLQGYTVEVLRQQPPDLVDFAVEYFTRLREARA (SEQ ID NO: 36)
SHIQIPPGLTELLQGYTVEVLRQQPPDLVEFLVEYFTRLREARA (SEQ ID NO: 37)
SHIQIPPGLTELLQGYTVEVLRQQPPDLVEFIVEYFTRLREARA (SEQ ID NO: 38)
SHIQIPPGLTELLQGYTVEVLRQQPPDLVEFVVEYFTRLREARA (SEQ ID NO: 39)
SHIQIPPGLTELLQGYTVEVLRQQPPDLVEFAVDYFTRLREARA
```

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:11), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:11 below. The skilled artisan will realize that in designing sequence variants of the AD sequence, one would desirably avoid changing any of the underlined residues, while conservative amino acid substitutions might be made for residues that are less critical for DDD binding. Table 3 shows potential conservative amino acid substitutions in the sequence of AKAP-IS (AD1, SEQ ID NO:19), similar to that shown for DDD1 (SEQ ID NO:16) in Table 2 above.

A limited number of such potential alternative AD moiety sequences are shown in SEQ ID NO:40 to SEQ ID NO:57 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

```
AKAP-IS
                                              (SEQ ID NO: 11)
QIEYLAKQIVDNAIQQA
```

TABLE 3

Conservative Amino Acid Substitutions in AD1 (SEQ ID NO: 11). Consensus sequence disclosed as SEQ ID NO: 95.

| Q | I | E | Y | L | A | K | Q | I | V | D | N | A | I | Q | Q | A |
|---|---|---|---|---|---|---|---|---|---|---|---|---|---|---|---|---|
| N | L | D | F | I |   | R | N |   |   | E | Q |   |   | N | N | L |
|   | V |   | T | V |   |   |   |   |   |   |   |   |   |   |   | I |
|   |   |   | S |   |   |   |   |   |   |   |   |   |   |   |   | V |

```
                                              (SEQ ID NO: 40)
NIEYLAKQIVDNAIQQA (SEQ ID NO: 41)
QLEYLAKQIVDNAIQQA (SEQ ID NO: 42)
QVEYLAKQIVDNAIQQA (SEQ ID NO: 43)
QIDYLAKQIVDNAIQQA (SEQ ID NO: 44)
QIEFLAKQIVDNAIQQA (SEQ ID NO: 45)
QIETLAKQIVDNAIQQA (SEQ ID NO: 46)
QIESLAKQIVDNAIQQA (SEQ ID NO: 47)
QIEYIAKQIVDNAIQQA (SEQ ID NO: 48)
QIEYVAKQIVDNAIQQA (SEQ ID NO: 49)
QIEYLARQIVDNAIQQA (SEQ ID NO: 50)
QIEYLAKNIVDNAIQQA (SEQ ID NO: 51)
QIEYLAKQIVENAIQQA (SEQ ID NO: 52)
QIEYLAKQIVDQAIQQA (SEQ ID NO: 53)
QIEYLAKQIVDNAINQA (SEQ ID NO: 54)
QIEYLAKQIVDNAIQNA (SEQ ID NO: 55)
QIEYLAKQIVDNAIQQL (SEQ ID NO: 56)
QIEYLAKQIVDNAIQQI (SEQ ID NO: 57)
QIEYLAKQIVDNAIQQV
```

Gold et al. (2006, Mol Cell 24:383-95) utilized crystallography and peptide screening to develop a SuperAKAP-IS sequence (SEQ ID NO:58), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL® constructs. Other alternative sequences that might be substituted for the AKAP-IS AD sequence are shown in SEQ ID NO:59-61. Substitutions relative to the AKAP-IS sequence are underlined. It is anticipated that, as with the AD2 sequence shown in SEQ ID NO:12, the AD moiety may also include the additional N-terminal residues cysteine and glycine and C-terminal residues glycine and cysteine.

```
SuperAKAP-IS
                        (SEQ ID NO: 58)
QIEYVAKQIVDYAIHQA

Alternative AKAP sequences
                        (SEQ ID NO: 59)
QIEYKAKQIVDHAIHQA (SEQ ID NO: 60)
QIEYHAKQIVDHAIHQA (SEQ ID NO: 61)
QIEYVAKQIVDHAIHQA
```

FIG. 2 of Gold et al. disclosed additional DDD-binding sequences from a variety of AKAP proteins, shown below.

RII-Specific AKAPs

```
AKAP-KL
                        (SEQ ID NO: 62)
PLEYQAGLLVQNAIQQAI

AKAP79
                        (SEQ ID NO: 63)
LLIETASSLVKNAIQLSI

AKAP-Lbc
                        (SEQ ID NO: 64)
LIEEAASRIVDAVIEQVK
```

RI-Specific AKAPs

```
AKAPce
                        (SEQ ID NO: 65)
ALYQFADRFSELVISEAL

RIAD
                        (SEQ ID NO: 66)
LEQVANQLADQIIKEAT

PV38
                        (SEQ ID NO: 67)
FEELAWKIAKMIWSDVF
```

Dual-Specificity AKAPs

```
AKAP7
                        (SEQ ID NO: 68)
ELVRLSKRLVENAVLKAV

MAP2D
                        (SEQ ID NO: 69)
TAEEVSARIVQVVTAEAV

DAKAP1
                        (SEQ ID NO: 70)
QIKQAAFQLISQVILEAT

DAKAP2
                        (SEQ ID NO: 71)
LAWKIAKMIVSDVMQQ
```

Stokka et al. (2006, Biochem J 400:493-99) also developed peptide competitors of AKAP binding to PKA, shown in SEQ ID NO:72-74. The peptide antagonists were designated as Ht31 (SEQ ID NO:72), RIAD (SEQ ID NO:73) and PV-38 (SEQ ID NO:74). The Ht-31 peptide exhibited a greater affinity for the RII isoform of PKA, while the RIAD and PV-38 showed higher affinity for RI.

```
Ht31
                        (SEQ ID NO: 72)
DLIEEAASRIVDAVIEQVKAAGAY

RIAD
                        (SEQ ID NO: 73)
LEQYANQLADQIIKEATE

PV-38
                        (SEQ ID NO: 74)
FEELAWKIAKMIWSDVFQQC
```

Hundsrucker et al. (2006, Biochem J 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

AKAP Peptide sequences

| | Peptide Sequence |
|---|---|
| AKAPIS | QIEYLAKQIVDNAIQQA (SEQ ID NO: 11) |
| AKAPIS-P | QIEYLAKQIPDNAIQQA (SEQ ID NO: 75) |
| Ht31 | KGADLIEEAASRIVDAVIEQVKAAG (SEQ ID NO: 76) |
| Ht31-P | KGADLIEEAASRIPDAPIEQVKAAG (SEQ ID NO: 77) |
| AKAP7δ-wt-pep | PEDAELVRLSKRLVENAVLKAVQQY (SEQ ID NO: 78) |
| AKAP7δ-L304T-pep | PEDAELVRTSKRLVENAVLKAVQQY (SEQ ID NO: 79) |
| AKAP7δ-L308D-pep | PEDAELVRLSKRDVENAVLKAVQQY (SEQ ID NO: 80) |
| AKAP7δ-P-pep | PEDAELVRLSKRLPENAVLKAVQQY (SEQ ID NO: 81) |
| AKAP7δ-PP-pep | PEDAELVRLSKRLPENAPLKAVQQY (SEQ ID NO: 82) |

TABLE 4-continued

AKAP Peptide sequences

| | Peptide Sequence |
|---|---|
| AKAP7δ-L314E-pep | PEDAELVRLSKRLVENAVEKAVQQY (SEQ ID NO: 83) |
| AKAP1-pep | EEGLDRNEEIKRAAFQIISQVISEA (SEQ ID NO: 84) |
| AKAP2-pep | LVDDPLEYQAGLLVQNAIQQAIAEQ (SEQ ID NO: 85) |
| AKAP5-pep | QYETLLIETASSLVKNAIQLSIEQL (SEQ ID NO: 86) |
| AKAP9-pep | LEKQYQEQLEEEVAKVIVSMSIAFA (SEQ ID NO: 87) |
| AKAP10-pep | NTDEAQEELAWKIAKMIVSDIMQQA (SEQ ID NO: 88) |
| AKAP11-pep | VNLDKKAVLAEKIVAEAIEKAEREL (SEQ ID NO: 89) |
| AKAP12-pep | NGILELETKSSKLVQNIIQTAVDQF (SEQ ID NO: 90) |
| AKAP14-pep | TQDKNYEDELTQVALALVEDVINYA (SEQ ID NO: 91) |
| Rab32-pep | ETSAKDNINIEEAARFLVEKILVNH (SEQ ID NO: 92) |

Residues that were highly conserved among the AD domains of different AKAP proteins are indicated below by underlining with reference to the AKAP IS sequence (SEQ ID NO:11). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
                            AKAP-IS
                                            (SEQ ID NO: 11)
                         QIEYLAKQIVDNAIQQA
```

Can et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:9. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
                                              (SEQ ID NO: 9)
    SHIQIPPGLTELLQGYTVEVLRQQPPDLVEFAVEYFTRLREARA
```

A modified set of conservative amino acid substitutions for the DDD1 (SEQ ID NO:9) sequence, based on the data of Carr et al. (2001) is shown in Table 5. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 2 and Table 3.

TABLE 5

Conservative Amino Acid Substitutions in DDD1 (SEQ ID NO: 9).
Consensus sequence disclosed as SEQ ID NO: 96.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   | N |   |   |   |   |   |   | S |   |   |   |   |   |   |   | I |   |   |   |   |
|   |   |   |   |   |   |   |   |   |   |   |   |   |   |   |   |   | L |   |   |   |   |
|   |   |   |   |   |   |   |   |   |   |   |   |   |   |   |   |   | A |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N |   |   |   |   |   | I | D |   |   |   | S |   | K |   | K |   |   |   | L |   | L |
|   |   |   |   |   |   | L |   |   |   |   |   |   |   |   |   |   |   |   | I |   | I |
|   |   |   |   |   |   | A |   |   |   |   |   |   |   |   |   |   |   |   | V |   | V |

The skilled artisan will realize that these and other amino acid substitutions in the DDD or AD amino acid sequences may be utilized to produce alternative species within the genus of AD or DDD moieties, using techniques that are standard in the field and only routine experimentation.

Alternative DNL® Structures

In certain alternative embodiments, DNL® constructs may be formed using alternatively constructed antibodies or antibody fragments, in which an AD moiety may be attached at the C-terminal end of the kappa light chain ($C_k$), instead of the C-terminal end of the Fc on the heavy chain. The alternatively formed DNL® constructs may be prepared as disclosed in Provisional U.S. Patent Application Ser. No. 61/654,310, filed Jun. 1, 2012, 61/662,086, filed Jun. 20, 2012, 61/673,553, filed Jul. 19, 2012, and 61/682,531, filed Aug. 13, 2012, the entire text of each incorporated herein by reference. The light chain conjugated DNL® constructs exhibit enhanced Fc-effector function activity in vitro and improved pharmacokinetics, stability and anti-lymphoma activity in vivo (Rossi et al., 2013, Bioconjug Chem 24:63-71).

$C_k$-conjugated DNL® constructs may be prepared as disclosed in Provisional U.S. Patent Application Ser. No. 61/654,310, 61/662,086, 61/673,553, and 61/682,531. Briefly, $C_k$-AD2-IgG, was generated by recombinant engineering, whereby the AD2 peptide was fused to the C-terminal end of the kappa light chain. Because the natural C-terminus of $C_K$ is a cysteine residue, which forms a disulfide bridge to $C_H1$, a 16-amino acid residue "hinge" linker was used to space the AD2 from the $C_K$-$V_H1$ disulfide bridge. The mammalian expression vectors for $C_k$-AD2-IgG-veltuzumab and $C_k$-AD2-IgG-epratuzumab were constructed using the pdHL2 vector, which was used previously for expression of the homologous $C_H3$-AD2-IgG modules. A 2208-bp nucleotide sequence was synthesized comprising the pdHL2 vector sequence ranging from the Bam HI restriction site within the $V_K/C_K$ intron to the Xho I restriction site 3' of the $C_k$ intron, with the insertion of the coding sequence for the hinge linker (EFPKPSTPPGSSGGAP, SEQ ID NO:93) and AD2, in frame at the 3'end of the coding sequence for $C_K$. This synthetic sequence was inserted into the IgG-pdHL2 expression vectors for veltuzumab and epratuzumab via Bam HI and Xho I restriction sites. Generation of production clones with SpESFX-10 were performed as described for the $C_H3$-AD2-IgG modules. $C_k$-AD2-IgG-veltuzumab and $C_k$-AD2-IgG-epratuzumab were produced by stably-transfected production clones in batch roller bottle culture, and purified from the supernatant fluid in a single step using Mab Select (GE Healthcare) Protein A affinity chromatography.

Following the same DNL® process described previously for 22-(20)-(20) (Rossi et al., 2009, Blood 113:6161-71), $C_k$-AD2-IgG-epratuzumab was conjugated with $C_H1$-DDD2-Fab-veltuzumab, a Fab-based module derived from veltuzumab, to generate the bsHexAb 22*-(20)-(20), where the 22* indicates the $C_k$-AD2 module of epratuzumab and each (20) symbolizes a stabilized dimer of veltuzumab Fab. The properties of 22*-(20)-(20) were compared with those of 22-(20)-(20), the homologous Fc-bsHexAb comprising $C_H3$-AD2-IgG-epratuzumab, which has similar composition and molecular size, but a different architecture.

Following the same DNL® process described previously for 20-2b (Rossi et al., 2009, Blood 114:3864-71), $C_k$-AD2-IgG-veltuzumab, was conjugated with IFNα2b-DDD2, a module of IFNα2b with a DDD2 peptide fused at its C-terminal end, to generate 20*-2b, which comprises veltuzumab with a dimeric IFNα2b fused to each light chain. The properties of 20*-2b were compared with those of 20-2b, which is the homologous Fc-IgG-IFNα.

Each of the bsHexAbs and IgG-IFNα were isolated from the DNL® reaction mixture by Mab Select affinity chromatography. The two $C_k$-derived prototypes, an anti-CD22/CD20 bispecific hexavalent antibody, comprising epratuzumab (anti-CD22) and four Fabs of veltuzumab (anti-CD20), and a CD20-targeting immunocytokine, comprising veltuzumab and four molecules of interferon-α2b, displayed enhanced Fc-effector functions in vitro, as well as improved pharmacokinetics, stability and anti-lymphoma activity in vivo, compared to their Fc-derived counterparts.

Amino Acid Substitutions

In alternative embodiments, the disclosed methods and compositions may involve production and use of proteins or peptides with one or more substituted amino acid residues. For example, the DDD and/or AD sequences used to make DNL® constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Pre-Targeting

Bispecific or multispecific antibodies may be of use in pretargeting techniques. In this case, one or more diagnostic and/or therapeutic agents may be conjugated to a targetable construct that comprises one or more haptens. The hapten is recognized by at least one arm of a bispecific or multispecific antibody that also binds to a tumor-associated antigen or other disease-associated antigen. In this case, the therapeutic agent binds indirectly to the antibodies, via the binding of the targetable construct. This process is referred to as pretargeting.

Pre-targeting is a multistep process originally developed to resolve the slow blood clearance of directly targeting antibodies, which contributes to undesirable toxicity to normal tissues such as bone marrow. With pre-targeting, a therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256, 395; Stickney et al., Cancer Res. 51:6650, 1991; Yuan et al., Cancer Res. 51:3119, 1991; U.S. Pat. Nos. 6,077,499; 7,011, 812; 7,300,644; 7,074,405; 6,962,702; 7,387,772; 7,052, 872; 7,138,103; 6,090,381; 6,472,511; 6,962,702; and 6,962, 702, each incorporated herein by reference.

A pre-targeting method of diagnosing or treating a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues and one or more haptens for binding, e.g., to a bispecific antibody. Exemplary haptens may include In-DTPA (indium-diethylene triamine pentaacetic acid) or HSG (histamine succinyl glycine). The targetable construct may also comprise one or more chelating moieties, such as DOTA (1,4,7,10-tetraazacyclododecane1,4,7,10-tetraacetic acid), NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties. Chelating moieties may be used, for example, to bind to a therapeutic and or diagnostic radionuclide, paramagnetic ion or contrast agent.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Immunoconjugates

Various embodiments may involve use of immunoconjugates, comprising an anti-Trop-2 antibody or antigen-binding fragment thereof attached to one or more diagnostic or therapeutic agents. In some embodiments, a drug or other agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetylmannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or Vκ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

Diagnostic Agents

Diagnostic agents may comprise any detectable agent that may be used to label a detection antibody, or to directly label a CTC, and are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds.

In certain embodiments, the fluorescent probe may be a DYLIGHT® dye (Thermo Fisher Scientific, Rockford, Ill.). The DYLIGHT® dye series are highly polar (hydrophilic), compatible with aqueous buffers, photostable and exhibit high fluorescence intensity. They remain highly fluorescent over a wide pH range and are preferred for various applications. However, the skilled artisan will realize that a variety of fluorescent dyes are known and/or are commercially available and may be utilized. Other fluorescent agents include, but are not limited to, dansyl chloride, rhodamine isothiocyanate, Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. (See, e.g., U.S. Pat. Nos. 5,800,992; 6,319,668.) These and other luminescent labels may be obtained from commercial sources such as Molecular Probes (Eugene, Oreg.), and EMD Biosciences (San Diego, Calif.).

Chemiluminescent labels of use may include luminol, isoluminol, an aromatic acridinium ester, an imidazole, an acridinium salt or an oxalate ester.

Therapeutic Agents

A wide variety of therapeutic reagents can be administered concurrently or sequentially with an anti-Trop-2 or other anti-TAA antibody. Alternatively, such agents may be conjugated to antibodies, for example, drugs, toxins, oligonucleotides, immunomodulators, hormones, hormone antagonists, enzymes, enzyme inhibitors, radionuclides, angiogenesis inhibitors, etc. Therapeutic agents include, for example, cytotoxic drugs such as vinca alkaloids, anthracyclines such as doxorubicin, 2-PDox or pro-2-PDox, gemcitabine, epipodophyllotoxins, taxanes, antimetabolites, alkylating agents, antibiotics, SN-38, COX-2 inhibitors, antimitotics, anti-angiogenic and pro-apoptotic agents, particularly doxorubicin, methotrexate, taxol, CPT-11, camptothecans, proteosome inhibitors, mTOR inhibitors, HDAC inhibitors, tyrosine kinase inhibitors, and others. Other useful anti-cancer cytotoxic drugs include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins, hormones, and the like. Suitable cytotoxic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable cytotoxic agents, such as experimental drugs, are known to those of skill in the art. In a preferred embodiment, conjugates of camptothecins and related compounds, such as SN-38, may be conjugated to anti-Trop-2 or other anti-TAA antibodies. In another preferred embodiment, gemcitabine is administered to the subject in conjunction with SN-38-hRS7 and/or $^{90}$Y-hPAM4.

A toxin can be of animal, plant or microbial origin. Toxins of use include ricin, abrin, ribonuclease (RNase), DNase I, Staphylococcal enterotoxin-A, pokeweed antiviral protein, onconase, gelonin, diphtheria toxin, *Pseudomonas* exotoxin, and *Pseudomonas* endotoxin. See, for example, Pastan et al., Cell 47:641 (1986), Goldenberg, Calif.—A Cancer Journal for Clinicians 44:43 (1994), Sharkey and Goldenberg, Calif.—A Cancer Journal for Clinicians 56:226 (2006). Additional toxins suitable for use are known to those of skill in the art and are disclosed in U.S. Pat. No. 6,077,499, the Examples section of which is incorporated herein by reference.

As used herein, the term "immunomodulator" includes a cytokine, a lymphokine, a monokine, a stem cell growth factor, a lymphotoxin, a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-α, TGF-β, insulin-like growth factor (ILGF), erythropoietin, thrombopoietin, tumor necrosis factor (TNF), TNF-α, TNF-β, a mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, interferon-λ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 and IL-25, LIF, kit-ligand, FLT-3, angiostatin, thrombospondin, endostatin, lymphotoxin, and the like.

Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{227}$Th, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Fm-255 and Th-227. Decay energies of useful alpha-particle-emitting radionuclides are preferably 2,000-10,000 keV, more preferably 3,000-8,000 keV, and most preferably 4,000-7,000 keV.

For example, $^{90}$Y, which emits an energetic beta particle, can be coupled to an antibody, antibody fragment or fusion protein, using diethylenetriaminepentaacetic acid (DTPA), or more preferably using DOTA. Methods of conjugating $^{90}$Y to antibodies or targetable constructs are known in the art and any such known methods may be used. (See, e.g., U.S. Pat. No. 7,259,249, the Examples section of which is incorporated herein by reference. See also Linden et al., Clin Cancer Res. 11:5215-22, 2005; Sharkey et al., J Nucl Med. 46:620-33, 2005; Sharkey et al., J Nucl Med. 44:2000-18, 2003.)

Additional potential therapeutic radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

In another embodiment, a radiosensitizer can be used in combination with a naked or conjugated antibody or antibody fragment. For example, the radiosensitizer can be used in combination with a radiolabeled antibody or antibody fragment. The addition of the radiosensitizer can result in enhanced efficacy when compared to treatment with the radiolabeled antibody or antibody fragment alone. Radiosensitizers are described in D. M. Goldenberg (ed.), CANCER THERAPY WITH RADIOLABELED ANTIBODIES, CRC Press (1995). Other typical radionsensitizers of interest for use with this technology include gemcitabine, 5-fluorouracil, and cisplatin, and have been used in combination with external irradiation in the therapy of diverse cancers.

Antibodies or fragments thereof that have a boron addend-loaded carrier for thermal neutron activation therapy will normally be affected in similar ways. However, it will be advantageous to wait until non-targeted immunoconjugate clears before neutron irradiation is performed. Clearance can be accelerated using an anti-idiotypic antibody that binds to the anti-cancer antibody. See U.S. Pat. No. 4,624,846 for a description of this general principle. For example, boron addends such as carboranes, can be attached to antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody. After administration of the antibody conjugate, a boron addend is activated by thermal neutron irradiation and converted to radioactive atoms which decay by alpha-emission to produce highly toxic, short-range effects.

Formulation and Administration

Where therapeutic antibodies are to be administered in vivo, suitable routes of administration may include, without limitation, oral, parenteral, rectal, transmucosal, intestinal administration, intramedullary, intrathecal, direct intraventricular, intravenous, intravitreal, intracavitary, intraperitoneal, or intratumoral injections. The preferred routes of administration are parenteral, more preferably intravenous. Alternatively, one may administer the compound in a local rather than systemic manner, for example, via injection of the compound directly into a solid or hematological tumor.

Antibodies can be formulated according to known methods to prepare pharmaceutically useful compositions, whereby the antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof In a preferred embodiment, the antibody is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino)ethanesulfonic acid (MES); 3-(N-morpholino)propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The antibody can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an antibody from such a matrix depends upon the molecular weight of the antibody, the amount of antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof Generally, the dosage of an administered antibody for humans will vary depending upon such factors as the patient's age, weight, height, sex, general medical condition and previous medical history. It may be desirable to provide the recipient with a dosage of antibody that is in the range of from about 0.3 mg/kg to 5 mg/kg as a single intravenous infusion, although a lower or higher dosage also may be administered as circumstances dictate. A dosage of 0.3-5 mg/kg for a 70 kg patient, for example, is 21-350 mg, or 12-206 mg/m$^2$ for a 1.7-m patient. The dosage may be repeated as needed, for example, once per week for 2-10 weeks, once per week for 8 weeks, or once per week for 4 weeks. It may also be given less frequently, such as every other week for several months, or monthly or quarterly for many months, as needed in a maintenance therapy. Preferred dosages may include, but are not limited to, 0.3 mg/kg, 0.5 mg/kg, 0.7 mg/kg, 1.0 mg/kg, 1.2 mg/kg, 1.5 mg/kg, 2.0 mg/kg, 2.5 mg/kg, 3.0 mg/kg, 3.5 mg/kg, 4.0 mg/kg, 4.5 mg/kg, and 5.0 mg/kg. More preferred dosages are 0.6 mg/kg for weekly administration and 1.2 mg/kg for less frequent dosing. Any amount in the range of 0.3 to 5 mg/kg may be used. The dosage is preferably administered multiple times, once a week. A minimum dosage schedule of 4 weeks, more preferably 8 weeks, more preferably 16 weeks or longer may be used, with the dose frequency dependent on toxic side-effects and recovery therefrom, mostly related to hematological toxicities. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off;

(vi) four weeks of therapy followed by one, two, three, four or five week off; (vii) five weeks of therapy followed by one, two, three, four or five week off; and (viii) monthly. The cycle may be repeated 2, 4, 6, 8, 10, or 12 times or more.

Alternatively, an antibody may be administered as one dosage every 2 or 3 weeks, repeated for a total of at least 3 dosages. Or, twice per week for 4-6 weeks. The dosage may be administered once every other week or even less frequently, so the patient can recover from any drug-related toxicities. Alternatively, the dosage schedule may be decreased, namely every 2 or 3 weeks for 2-3 months. The dosing schedule can optionally be repeated at other intervals and dosage may be given through various parenteral routes, with appropriate adjustment of the dose and schedule.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. In preferred embodiments, the method of the invention is used to inhibit growth, progression, and/or metastasis of cancers, in particular those listed above.

Kits

Various embodiments may concern kits containing components suitable for detecting Trop-2 positive CTCs in a patient. Exemplary kits may contain at least one anti-Trop-2 antibody as described herein. In certain embodiments, the antibody may be conjugated to at least one diagnostic agent. In alternative embodiments, a second antibody that binds to a Trop-2 positive CTC may be included. The second antibody may bind to a different epitope of Trop-2 or to a different TAA, and may be labeled with at least one diagnostic agent. In certain embodiments, an anti-Trop-2 antibody or antigen binding fragment thereof may be provided in the form of a prefilled syringe or vial containing a sterile, liquid formulation or lyophilized preparation of antibody (e.g., Kivitz et al., Clin. Ther. 2006, 28:1619-29).

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions for use of the kit.

EXAMPLES

The examples below are illustrative of embodiments of the current invention and are not limiting to the scope of the claims.

Example 1

Cell Binding Assay of Anti-Trop-2 Antibodies

Two different murine monoclonal antibodies against human Trop-2 were obtained. The first, 162-46.2, was purified from a hybridoma (ATCC, HB-187) grown up in roller-bottles. A second antibody, MAB650, was purchased from R&D Systems (Minneapolis, Minn.). For a comparison of binding, the Trop-2-positive human gastric carcinoma, NCI-N87, was used as the target. Cells ($1.5 \times 10^5$/well) were plated into 96-well plates the day before the binding assay. The following morning, a dose/response curve was generated with 162-46.2, MAB650, and murine RS7 (0.03 to 66 nM) (not shown). These primary antibodies were incubated with the cells for 1.5 h at 4° C. Wells were washed and an anti-mouse-HRP secondary antibody was added to all the wells for 1 h at 4° C. Wells are washed again followed by the addition of a luminescence substrate. Plates were read using Envision plate reader and values are reported as relative luminescent units.

All three antibodies had similar $K_D$-values of 0.57 nM for RS7, 0.52 nM for 162-46.2 and 0.49 nM for MAB650 (not shown). However, when comparing the maximum binding ($B_{max}$) of 162-46.2 and MAB650 to RS7 they were reduced by 25% and 50%, respectively ($B_{Max}$ 11,250 for RS7, 8,471 for 162-46.2 and 6,018 for MAB650) indicating different binding properties in comparison to RS7 (not shown).

Example 2

Collection and Storage of Blood Samples

Ten mL blood samples are drawn from each of 10 healthy donors and 20 patients with metastatic breast cancer and dispensed into a CELLSAVE™ Preservative tube (Jassen Diagnostics LLC, Raritan, N.J.). The samples are stored at RT and processed within 72 h of blood collection (Allard et al., 2004, Clin Cancer Res, 10: 6897). Alternatively, 10 mL of blood samples are drawn into a CYTOCHEX® Blood collection tube (Streck, Omaha, Nebr.), maintained at RT, and processed within 7 days (Ng et al., 2012 J Immunol Methods, 385: 79). Blood can also be drawn into 10 mL K2EDTA VACUTAINER® (BD, Waltham, Mass.), fixed with the LIQUIDBIOPSY® fixative (Cynvenio Biosystems, Westlake Village, Calif.)) within 4 h of collection, stored at room temperature, and processed within 96 h of fixation.

Example 3

Spiking of cancer cells in blood samples from healthy donors

SK-BR-3 and BxPC-3 cells, both expressing high levels of Trop-2, are cultured in their designated medium, and harvested using trypsin. The viability and cell number of the resulting cell suspensions are assessed by Guava EASY-CYTE™ flow cytometer. The cell suspensions are used only when their viability exceeds 90%. The number of cells spiked into normal serum is from 1 to 100 per mL. Cancer cells that express moderate levels of Trop-2, for example, MCF-7, LoVo, and LS 174 T, low levels of Trop-2, for example, HT-29, or are negative for Trop-2, for example, A549 and H460, can also be used to spike blood samples.

Example 4

Isolation of Epithelial Cancer Cells from Spiked Blood Samples with the Use of a Magnetic Device Blood samples spiked with epithelial cancer cells are incubated with biotinylated tri-Fab hRS7 (biotin-E1/3, prepared by the DNL® technique described above), and ferrofluids coated with streptavidin (FF-SV) to immunomagnetically enrich epithelial cells. Briefly, 7.5 mL of a blood sample containing a known number of spiked BxPC-3 or SK-BR-3 are mixed with 6 mL of buffer, and centrifuged at 800×g for 10 min. After removing the plasma and buffer layer, biotin-E1/3 and FF-SV are added and incubated for 1 h. Subsequently, unlabeled cells are removed from labeled cells following magnetic separation. Cells labeled with biotin-E1/3 are then detached from FF-SV with a further wash and centrifugation, and are analyzed by flow cytometry after labeling with DAPI, PE-anti-CK18, and APC-anti-CD45. Nucleated cells lacking CD45 and expressing cytokeratin (CK8, CK18, CK19) are generally defined as CTCs (Swaby & Cristofanilli, 2011, BMC Medicine, 9: 43).

Example 5

Isolation of Epithelial Cancer Cells from Spiked Blood Samples without the Use of a Magnetic Device Blood samples spiked with epithelial cancer cells are incubated with biotin-E1/3 in a microvortex-generating herringbone-chip (HP-Chip) chemically modified with avidin as described by Stott et al (2010, PNAS, 107: 18392), or more preferably, are incubated with biotin-E1/3 for 1 h before adding to NanoVelcro chips functionalized with streptavidin as described by Lu et al. (2013, Methods, 64: 144). After rinsing away the unbound cells, the bound cells are analyzed for CTCs as described in Example 3.

Example 6

Detection of Epithelial Cancer Cells from Spiked Blood Samples without Prior Enrichment Red blood cells in blood samples spiked with BxPC-3 are lysed with ammonium chloride, and centrifuged. The cell pellets are collected and incubated with FITC-labeled E1/3. The live cells in suspension are then applied to a poly-lysine-treated slide and analyzed with a laser scanning cytometer (Pachmann et al., 2005, Breast Cancer Res, 7: R975). Alternatively, the cell pellets collected after lysis of red blood cells are incubated with a cocktail comprising biotinylated E1/3 and one or more of other biotinylated DNL® conjugates in the presence of FITC-labeled avidin. The live cells in suspension are then analyzed by laser scanning cytometer.

Example 7

Detection of Epithelial Cancer Cells from Spiked Blood Samples Using a Bispecific Construct Targeting Both Trop-2 and EGFR Blood samples spiked with BxPC-3 cells, which express high levels of both Trop-2 and EGFR, are incubated with a biotinylated bispecific Tri-Fab, designated (E1)-225, and ferrofluids coated with streptavidin (FF-SV), as described in Example 4. (E1)-225 is generated by conjugating $C_H1$-DDD2-Fab-hRS7 to $C_H1$-AD2-Fab-c225, thus providing bivalent and monovalent binding to Trop-2 and EGFR, respectively. When compared with the enrichment using only monospecific hRS7 or c225 (cetuximab), the bispecific (E1)-225 is able to capture more BxPC-3 spiked into the blood samples, with less contamination of CD45-positive white blood cells.

Example 8

Detection of Trop-2⁺ CTCs Using LIQUIDBIOPSY® System

A LIQUIDBIOPSY® instrument (Cat. No. A28188), LIQUIDBIOPSY® Blood Collection Kit (Cat. No. A28171) and LIQUIDBIOPSY® Reagents and Consumables Kits (Cat. Nos. A28186, A28187) are obtained from Life Technologies, ThermoFisher (Grand Island, N.Y.). The LIQUIDBIOPSY® kits includes a stabilization protocol for whole-blood samples, allowing unrefrigerated shipping of samples (96-hour window), as well as buffers, reagents, vials, elution tubes, and flow cells to process blood samples.

The humanized RS7 (hRS7) monoclonal antibody (sacituzumab) is biotinylated using the protocols and reagents provided with the Reagents and Consumables kit. Biotinylated hRS7 (sacituzumab) is used in place of the anti-EpCAM biotinylated antibody provided with the Reagents and Consumables Kit. Alternatively, anti-TROP-2 Biotinylated Antibody (Cat. No. BAF650, R&D Systems, Minneapolis, Minn.) is used in place of anti-EpCAM.

Circulating tumor cells from the blood of patients with solid tumors are isolated using the anti-TROP-2 biotinylated antibody and the instrument and reagents discussed above, according to the manufacturer's instructions. Isolated tumor cells are released from the slide, and confirmed by flow cytometry after labeling with DAPI, PE-anti-CK18, and APC-anti-CD45, as described in Example 3. Released cells from a second blood specimen are cultured, and a colony of live cells is obtained, which are isolated and analyzed by FISH for the copy number of Trop-2 and chromosome-1 using specific probes available from Empire Genomics (Buffalo, N.Y.). FIG. 1 and FIG. 2 are representative results obtained in MCF-7 (Trop-2-positive) and A549 (Trop-2-negative) cells, showing 3 and 2 copies of the Trop-2 gene, respectively. In addition, the copy number of topoisomerase-I (TOP1) and chromosome-20 are also determined using specific probes provided by Abnova (Taipei, Taiwan) and documented. FIG. 3 and FIG. 4 are representative results obtained in MCF-7 and A549 cells, showing 7 and 3 copies of the TOP1 gene, respectively. The simultaneous detection and quantitation of copy numbers of Trop-2 and TOP1 allow the determination of cancer cells that also express TOP1, which would indicate which patient tumors may be particularly responsive or resistant to a TOP1-inhibitor therapy, such as with irinotecan. This is particularly useful when using sacituzumab govitecan (IMMU-132), which targets Trop-2-expressing cancer cells and delivers SN-38 selectively to such cells. Recovery of tumor cells from blood samples is compared using anti-Trop-2 hRS7 antibody versus the anti-EpCAM antibody provided with the kit. Surprisingly, recovery of CTCs is higher with the anti-Trop-2 antibody than the anti-EpCAM antibody.

Example 9

Isolation of Trop-2⁺ CTCs with IMAG™ Magnetic Particles

Purified mouse anti-human Trop-2 antibody is prepared from clone 162-46, purchased from BD Pharmingen (San Jose, Calif.). The anti-Trop-2 antibody is biotinylated as described in Example 7. IMAG™ magnetic particles (Streptavidin Particles Plus—DM) and a BD IMAG™ Cell Separation Magnet are purchased from BD Biosciences (San Jose, Calif.). Ten ml plastic whole blood tubes spray-coated with K2EDTA (Cat. No. 366643) are also purchased from BD.

For separation and analysis of CTCs, ten mL blood samples are drawn from patients with lung cancer and stored in K2EDTA tubes. Mononuclear cells are obtained by density gradient centrifugation using Ficoll-Hypaque solution. Protocols for positive selection of CTCs from Ficoll-Hypaque are as disclosed in BD Technical Data Sheet Streptavidin Particles Plus—DM Material Number: 557812. After the final wash step on the BD IMAG™ magnet, the released cells are resuspended in buffer.

The cells are stained with fluorescently labeled anti-cytokeratin, fluorescently labeled affinity purified goat anti-TROP-2, DAPI and/or anti-CD45. Subsequent immunofluorescence images are taken of the captured cells, followed by comprehensive computer aided analysis based on fluorescence intensities and cell morphology.

Example 10

Detection of Trop-2$^+$ CTCs and Treatment of Metastatic Trop-2 Expressing Cancer A CELLSEARCH® system and Circulating Tumor Cell Kit are obtained Veridex LLC (Raritan, N.J.). A 7.5 ml blood sample is collected from a 65 year-old male with suspected NSCLC and stored in a CellSave tube (Veridex LLC). The anti-Trop-2 hRS7 antibody is substituted for the anti-EpCAM antibody provided with the CELLSEARCH® kit. The blood sample is mixed with magnetic nanoparticles conjugated to anti-Trop-2 antibody. Cells are stained with fluorescently labeled anti-CD45 and anti-CK antibodies and cell nuclei are fluorescently labeled with DAPI nuclear dye. A strong magnetic field is generated in the CELLSEARCH® system and used to separate cells bound to the magnetic nanoparticles, which are then analyzed by FISH to determine Trop-2 copy number, as described in Example 7 above. The results show the presence of circulating Trop-2$^+$ tumor cells, with 4 copies of Trop-2 per cell. The presence of high copy numbers of Trop-2 in the CTCs indicates that the patient is a good candidate for therapy with anti-Trop-2 antibodies.

Further clinical workup shows the presence of stage IIIB NSCLC (squamous cell carcinoma). Initial treatment of caboplatin/etoposide (3 mo) in concert with 7000 cGy XRT results in a response lasting 10 mo. The patient is then started on Tarceva maintenance therapy, which he continues until he was considered for IMMU-132 (hRS7-CL2A-SN-38) trial, in addition to undergoing a lumbar laminectomy. He receives the first dose of IMMU-132 after 5 months of Tarceva, presenting at the time with a 5.6-cm lesion in the right lung with abundant pleural effusion. He completes his 6$^{th}$ dose two months later when the first CT shows the primary target lesion reduced to 3.2 cm. Periodic assays for Trop-2$^+$ CTCs show a substantial reduction in CTC number following treatment with IMMU-132.

This Example shows the feasibility of selecting for patients who are responsive to therapy with IMMU-132 or another therapeutic anti-Trop-2 antibody, by assaying for Trop-2$^+$ CTCs in the individual patient's blood and/or determining Trop-2 copy number in CTCs. The Example further demonstrates the feasibility of monitoring relative levels of Trop-2$^+$ CTCs as an indicator of the efficacy of anti-Trop-2 based therapies. Preferably, patients who show a positive response, including but not limited to a complete response (CR), partial response (PR) and/or stable disease (SD) will show a decrease in levels of Trop-2$^+$ CTCs of at least 50%, at least 60%, at least 70%, at least 80%, at least 90%, at least 95%, at least 98% or at least 99%. Where the treatment is highly efficacious and results in complete response, a decrease of 100% in Trop-2$^+$ CTCs may be observed.

Example 11

Isolation and Detection of Trop-2$^+$ CTCs with a VerIFAST System

A VerIFAST system as disclosed in Casavant et al. (2013, Lab Chip 13:391-6; 2014, Lab Chip 14:99-105) is used to detect Trop-2+ CTCs in TNBC. 7.5 ml blood samples are collected from a series of patients with suspected TNBC or control normal individuals and stored in CellSave tubes (Veridex LLC). Biotinylated anti-Trop-2 hRS7 antibody is prepared as disclosed in Casavant et al. (2013, Lab Chip 13:391-6). The blood samples are mixed with biotinylated anti-Trop-2 antibody and streptavidin-conjugated PMPs (Casavant et al., 2013, Lab Chip 13:391-6) and CTCs are separated with the VerIFAST platform and a handheld magnet. Cells are stained for tumor markers and cell nuclei are fluorescently labeled with DAPI nuclear dye. The results show the presence of circulating Trop-2$^+$ tumor cells in blood samples from individuals with TNBC, but not control normal individuals.

Example 12

Clinical Trials with IMMU-132 Anti-Trop-2 ADC Comprising hRS7 Antibody Conjugated to SN-38

Summary

The present Example reports results from a phase I clinical trial and ongoing phase II extension with IMMU-132 (sacituzumab govitecan), an antibody-drug conjugate (ADC) of the internalizing, humanized, hRS7 anti-Trop-2 antibody conjugated by a pH-sensitive linker to SN-38 (mean drug-antibody ratio=7.6). Trop-2 is a type I transmembrane, calcium-transducing, protein expressed at high density (~1×10$^5$), frequency, and specificity by many human carcinomas, with limited normal tissue expression. Preclinical studies in nude mice bearing Capan-1 human pancreatic tumor xenografts have revealed IMMU-132 is capable of delivering as much as 136-fold more SN-38 to tumor than derived from a maximally tolerated irinotecan therapy (not shown).

The present Example reports the initial Phase I trial of 25 patients (pts) who had failed multiple prior therapies (some including topoisomerase-I/II inhibiting drugs), and the ongoing Phase II extension now reporting on 69 pts, including in colorectal (CRC), small-cell and non-small cell lung (SCLC, NSCLC, respectively), triple-negative breast (TNBC), pancreatic (PDC), esophageal, and other cancers.

As discussed in detail below, Trop-2 was not detected in serum, but was strongly expressed (≥2$^+$) in most archived tumors. In a 3+3 trial design, IMMU-132 was given on days 1 and 8 in repeated 21-day cycles, starting at 8 mg/kg/dose, then 12 and 18 mg/kg before dose-limiting neutropenia. To optimize cumulative treatment with minimal delays, phase II is focusing on 8 and 10 mg/kg (n=30 and 14, respectively).

In 49 pts reporting related AE at this time, neutropenia ≥G3 occurred in 28% (4% G4). Most common non-hematological toxicities initially in these pts have been fatigue (55%; ≥G3=9%), nausea (53%;≥G3=0%), diarrhea (47%; ≥G3=9%), alopecia (40%), and vomiting (32%;≥G3=2%). Homozygous UGT1A1 *28/*28 was found in 6 pts, 2 of whom had more severe hematological and GI toxicities. In the Phase I and the expansion phases, there are now 48 pts (excluding PDC) who are assessable by RECIST/CT for best response. Seven (15%) of the patients had a partial response (PR), including patients with CRC (N=1), TNBC (N=2), SCLC (N=2), NSCLC (N=1), and esophageal cancers (N=1), and another 27 pts (56%) had stable disease (SD), for a total of 38 pts (79%) with disease response; 8 of 13 CT-assessable PDC pts (62%) had SD, with a median time to progression (TTP) of 12.7 wks compared to 8.0 weeks in their last prior therapy. The TTP for the remaining 48 pts is 12.6+ wks (range 6.0 to 51.4 wks). Plasma CEA and CA19-9 correlated with responses. No anti-hRS7 or anti-SN-38 antibodies were detected despite dosing over months. The conjugate cleared from the serum within 3 days, consistent with in vivo animal studies where 50% of the SN-38 was released daily, with >95% of the SN-38 in the serum being bound to the IgG in a non-glucoronidated form, and at concentrations as much as 100-fold higher than SN-38 reported in patients given irinotecan. These results show that the hRS7-SN-38-containing ADC is therapeutically active in metastatic solid cancers, with manageable diarrhea and neutropenia.

Pharmacokinetics

Two ELISA methods were used to measure the clearance of the IgG (capture with anti-hRS7 idiotype antibody) and the intact conjugate (capture with anti-SN-38 IgG/probe with anti-hRS7 idiotype antibody). SN-38 was measured by HPLC. Total IMMU-132 fraction (intact conjugate) cleared more quickly than the IgG (not shown), reflecting known gradual release of SN-38 from the conjugate. HPLC determination of SN-38 (Unbound and TOTAL) showed >95% the SN-38 in the serum was bound to the IgG. Low concentrations of SN-38G suggest SN-38 bound to the IgG is protected from glucoronidation. Comparison of ELISA for conjugate and SN-38 HPLC revealed both overlap, suggesting the ELISA is a surrogate for monitoring SN-38 clearance.

A summary of the dosing regiment and patient poll is provided in Table 6.

TABLE 6

Clinical Trial Parameters

| | |
|---|---|
| Dosing regimen | Once weekly for 2 weeks administered every 21 days for up to 8 cycles. In the initial enrollment, the planned dose was delayed and reduced if ≥G2 treatment-related toxicity; protocol was amended to dose delay and reduction only in the event of ≥G3 toxicity. |
| Dose level cohorts | 8, 12, 18 mg/kg; later reduced to an intermediate dose level of 10 mg/kg. |
| Cohort size | Standard Phase I [3 + 3] design; expansion includes 15 patients in select cancers. |
| DLT | G4 ANC ≥ 7 d; ≥G3 febrile neutropenia of any duration; G4 Plt ≥ 5 d; G4 Hgb; Grade 4 N/V/D any duration/G3 N/V/D for >48 h; G3 infusion-related reactions; related ≥G3 non-hematological toxicity. |
| Maximum Acceptable Dose (MAD) | Maximum dose where ≥2/6 patients tolerate 1st 21-d cycle w/o delay or reduction or ≥G3 toxicity. |

TABLE 6-continued

Clinical Trial Parameters

| | |
|---|---|
| Patients | Metastatic colorectal, pancreas, gastric, esophageal, lung (NSCLC, SCLC), triple-negative breast (TNBC), prostate, ovarian, renal, urinary bladder, head/neck, hepatocellular. Refractory/relapsed after standard treatment regimens for metastatic cancer. Prior irinotecan-containing therapy NOT required for enrollment. No bulky lesion >5 cm. Must be 4 weeks beyond any major surgery, and 2 weeks beyond radiation or chemotherapy regimen. Gilbert's disease or known CNS metastatic disease are excluded. |

Clinical Trial Status

A total of 69 patients (including 25 patients in Phase I) with diverse metastatic cancers having a median of 3 prior therapies were reported. Eight patients had clinical progression and withdrew before CT assessment. Thirteen CT-assessable pancreatic cancer patients were separately reported. The median TTP (time to progression) in PDC patients was 11.9 wks (range 2 to 21.4 wks) compared to median 8 wks TTP for the preceding last therapy.

A total of 48 patients with diverse cancers had at least 1 CT-assessment from which Best Response (not shown) and Time to Progression (TTP; not shown) were determined. To summarize the Best Response data, of 8 assessable patients with TNBC (triple-negative breast cancer), there were 2 PR (partial response), 4 SD (stable disease) and 2 PD (progressive disease) for a total response [PR+SD] of 6/8 (75%). For SCLC (small cell lung cancer), of 4 assessable patients there were 2 PR, 0 SD and 2 PD for a total response of 2/4 (50%). For CRC (colorectal cancer), of 18 assessable patients there were 1 PR, 11 SD and 6 PD for a total response of 12/18 (67%). For esophageal cancer, of 4 assessable patients there were 1 PR, 2 SD and 1 PD for a total response of 3/4 (75%). For NSCLC (non-small cell lung cancer), of 5 assessable patients there were 1 PR, 3 SD and 1 PD for a total response of 4/5 (80%). Over all patients treated, of 48 assessable patients there were 7 PR, 27 SD and 14 PD for a total response of 34/48 (71%). These results demonstrate that the anti-TROP-2 ADC (hRS7-SN-38) showed significant clinical efficacy against a wide range of solid tumors in human patients.

The reported side effects of therapy (adverse events) are summarized in Table 7. The therapeutic efficacy of hRS7-SN-38 was achieved at dosages of ADC showing an acceptably low level of adverse side effects. By comparison, patients receiving a dosage of irinotecan (125 mg/m$^2$ weekly×4, Q6W) showed a much higher incidence of adverse effects, with 38% incidence of grade 3/4 diarrhea, 31% neutropenia and 8% neutropenic fever/infection.

TABLE 7

Related Adverse Events Listing for IMMU-132,
Starting does of 8 or 10 mg/kg
Criteria: Grade 3-4 Adverse Event for >5% or any
Grade 3 or 4 Adverse Event (N = 123 patients)

| | Grade 3 | Grade 4 |
|---|---|---|
| Neutropenia | 22 (18%) | 7 (6%) |
| Febrile Neutropenia | 3 (2%) | 2 (2%) |
| Diarrhea | 4 (3%) | 0 |
| Anemia | 7 (6%) | 0 |
| Fatigue | 6 (5%) | 0 |
| Vomiting | 2 (2%) | 0 |
| WBC Decrease | 2 (2%) | 0 |
| Lymphocyte Decrease | 2 (2%) | 0 |
| Asthenia | 1 (1%) | 0 |

TABLE 7-continued

Related Adverse Events Listing for IMMU-132,
Starting does of 8 or 10 mg/kg
Criteria: Grade 3-4 Adverse Event for >5% or any
Grade 3 or 4 Adverse Event (N = 123 patients)

|  | Grade 3 | Grade 4 |
| --- | --- | --- |
| Dizziness | 1 (1%) | 0 |
| Urinary Tract Infection | 1 (1%) | 0 |
| Alopecia | — | — |

Data on dose reduction is also summarized. Of 76 patients starting at a dose of 8 mg/kg, 12 (16%) were provided with a dose reduction. Of 33 patients at a starting dose of 10 mg/kg, 5 (15%) were provided with a dose reduction. Of 9 patients at a starting dose of 12 mg/kg, 6 (67%) were provided with a dose reduction. Of 3 patients at a starting dose of 18 mg/kg, 3 (100%) were provided with a dose reduction. We conclude that at 8 and 10 mg/kg, there were few dose reductions, reflecting a mild, predictable and manageable toxicity profile at therapeutic levels of ADC. Currently, 425 serum samples from 148 patients have been analyzed and no evidence of an antibody response to IMMU-132 has been detected, even after repeated administration, with some patients receiving more than 20 doses of ADC.

Of 46 assessable patients with TNBC treated to date (Phase I and II), an objective response was seen in 12 patients (26%), with disease control in 34 patients (74%), a clinical benefit ratio (CR+PR+(SD≥6 mo)] of 46% and a clinical benefit ratio (CR+PR+(SD≥4 mo)] of 63%.

Of 19 assessable patients with NSCLC treated to date, an objective response was seen in 6 patients (32%), with disease control in 14 patients (74%), and a clinical benefit ratio (CR+PR+(SD≥4 mo)] of 59%.

Of 20 assessable patients with SCLC treated to date, an objective response was seen in 6 patients (30%), with disease control in 11 patients (55%), a clinical benefit ratio (CR+PR+(SD≥6 mo)] of 37% and a clinical benefit ratio (CR+PR+(SD≥4 mo)] of 55%.

Of 16 assessable patients with EAC treated to date, an objective response was seen in 2 patients (13%), with disease control in 9 patients (56%), and a clinical benefit ratio (CR+PR+(SD≥4 mo)] of 44%.

Exemplary partial responses to the anti-Trop-2 ADC were confirmed by CT data (not shown). As an exemplary PR in CRC, a 62-year-old woman first diagnosed with CRC underwent a primary hemicolectomy. Four months later, she had a hepatic resection for liver metastases and received 7 mos of treatment with FOLFOX and 1 mo 5FU. She presented with multiple lesions primarily in the liver (3+ Trop-2 by immunohistology), entering the hRS7-SN-38 trial at a starting dose of 8 mg/kg about 1 year after initial diagnosis. On her first CT assessment, a PR was achieved, with a 37% reduction in target lesions (not shown). The patient continued treatment, achieving a maximum reduction of 65% decrease after 10 months of treatment (not shown) with decrease in CEA from 781 ng/mL to 26.5 ng/mL), before progressing 3 months later.

As an exemplary PR in NSCLC, a 65-year-old male was diagnosed with stage IIIB NSCLC (sq. cell). Initial treatment of caboplatin/etoposide (3 mo) in concert with 7000 cGy XRT resulted in a response lasting 10 mo. He was then started on Tarceva maintenance therapy, which he continued until he was considered for IMMU-132 trial, in addition to undergoing a lumbar laminectomy. He received first dose of IMMU-132 after 5 months of Tarceva, presenting at the time with a 5.6 cm lesion in the right lung with abundant pleural effusion. He had just completed his 6$^{th}$ dose two months later when the first CT showed the primary target lesion reduced to 3.2 cm (not shown).

As an exemplary PR in SCLC, a 65-year-old woman was diagnosed with poorly differentiated SCLC. After receiving carboplatin/etoposide (Topo-II inhibitor) that ended after 2 months with no response, followed with topotecan (Topo-I inhibitor) that ended after 2 months, also with no response, she received local XRT (3000 cGy) that ended 1 month later. However, by the following month progression had continued. The patient started with IMMU-132 the next month (12 mg/kg; reduced to 6.8 mg/kg; Trop-2 expression 3+), and after two months of IMMU-132, a 38% reduction in target lesions, including a substantial reduction in the main lung lesion occurred (not shown). The patient progressed 3 months later after receiving 12 doses.

These results are significant in that they demonstrate that the anti-Trop-2 ADC was efficacious, even in patients who had failed or progressed after multiple previous therapies.

In conclusion, at the dosages used, the primary toxicity was a manageable neutropenia, with few Grade 3 toxicities. IMMU-132 showed evidence of activity (PR and durable SD) in relapsed/refractory patients with triple-negative breast cancer, small cell lung cancer, non-small cell lung cancer, colorectal cancer and esophageal cancer, including patients with a previous history of relapsing on topoisomerase-I inhibitor therapy. These results show efficacy of the anti-Trop-2 ADC in a wide range of cancers that are resistant to existing therapies.

It will be apparent to those skilled in the art that various modifications and variations can be made to the products, compositions, methods and processes of this invention. Thus, it is intended that the present invention cover such modifications and variations, provided they come within the scope of the appended claims and their equivalents.

What is claimed is:

1. A method of treating Trop-2+ tumors consisting of:
   a) exposing an anti-Trop-2 antibody or antigen-binding fragment thereof to blood from a subject suspected of having a Trop-2+ cancer;
   b) allowing the anti-Trop-2 antibody or fragment thereof to bind to Trop-2+ circulating tumor cells (CTCs);
   c) detecting CTCs bound to the anti-Trop-2 antibody or fragment thereof; and
   d) treating the subject with an anti-Trop-2 antibody conjugated to at least one therapeutic agent.

2. A method of treating Trop-2+ tumors consisting of:
   a) exposing an anti-Trop-2 antibody or antigen-binding fragment thereof to blood from a human subject suspected of having a Trop-2+ cancer;
   b) allowing the anti-Trop-2 antibody or fragment thereof to bind to Trop-2+ circulating tumor cells (CTCs);
   c) detecting CTCs bound to the anti-Trop-2 antibody or fragment thereof;
   d) analyzing the copy number of Trop-2 in the CTCs; and
   e) treating the human subject with an anti-Trop-2 antibody conjugated to at least one therapeutic agent.

3. The method of claim 2, wherein the presence of Trop-2+ CTCs with a high copy number of Trop-2, wherein a high copy number is 3 or more per cell, is predictive of response to a therapeutic anti-Trop-2 antibody.

4. A method of treating Trop-2+ tumors consisting of:
   a) exposing an anti-Trop-2 antibody or antigen-binding fragment thereof to blood from a human subject suspected of having a Trop-2+ cancer;
   b) allowing the anti-Trop-2 antibody or fragment thereof to bind to Trop-2+ circulating tumor cells (CTCs);
   c) detecting CTCs bound to the anti-Trop-2 antibody or fragment thereof;
   d) treating the human subject with an anti-Trop-2 antibody conjugated to at least one therapeutic agent; and e) monitoring the presence of Trop-2⁺ CTCs in the circulation to determine the response of the tumor to therapeutic anti-Trop-2 antibody.

5. The method of claim 1, wherein the therapeutic agent is selected from the group consisting of an antibody, an antibody fragment, a drug, a toxin, a hormone, an immunomodulator, a pro-apoptotic agent, an anti-angiogenic agents, a boron compound, a photoactive agent and a radionuclide.

6. The method of claim 5, wherein the drug is selected from the group consisting of an anthracycline, a camptothecin, a tubulin inhibitor, a maytansinoid, a calicheamycin, an auristatin, a nitrogen mustard, an ethylenimine derivative, an alkyl sulfonate, a nitrosourea, a triazene, a folic acid analog, a taxane, a COX-2 inhibitor, a pyrimidine analog, a purine analog, an antibiotic, an enzyme inhibitor, an epipodophyllotoxin, a platinum coordination complex, a vinca alkaloid, a substituted urea, a methyl hydrazine derivative, an adrenocortical suppressant, a hormone antagonist, an antimetabolite, an alkylating agent, an antimitotic, an anti-angiogenic agent, a tyrosine kinase inhibitor, an mTOR inhibitor, a heat shock protein (HSP90) inhibitor, a proteosome inhibitor, an HDAC inhibitor, and a pro-apoptotic agent.

7. The method of claim 5, wherein the drug is selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyano-morpholino doxorubicin, doxorubicin glucuronide, endostatin, epirubicin glucuronide, erlotinib, estramustine, epidophyllotoxin, erlotinib, entinostat, estrogen receptor binding agents, etoposide (VP 16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839.

8. The method of claim 5, wherein the drug is selected from the group consisting of SN-38, pro-2-pyrrolinodoxorubicin (pro-2-PDox), paclitaxel, calichemicin, DM1, DM3, DM4, MMAE, MMAD and MMAF.

9. The method of claim 1, wherein the cancer is resistant to treatment with at least one anti-cancer therapy.

10. The method of claim 1, wherein the cancer is pancreatic cancer.

11. The method of claim 5, wherein the radionuclide is selected from the group consisting of $^{11}C$, $^{13}N$, $^{15}O$, $^{32}P$, $^{33}P$, $^{47}Sc$, $^{51}Cr$, $^{57}Co$, $^{58}Co$, $^{59}Fe$, $^{62}Cu$, $^{67}Cu$, $^{67}Ga$, $^{67}Ga$, $^{75}Br$, $^{75}Se$, $^{75}Se$, $^{76}Br$, $^{77}As$, $^{77}Br$, $^{80m}Br$, $^{89}Sr$, $^{90}Y$, $^{95}Ru$, $^{97}Ru$, $^{99}Mo$, $^{99m}Tc$, $^{103m}Rh$, $^{103}Ru$, $^{105}Rh$, $^{105}Ru$, $^{107}Hg$, $^{109}Pd$, $^{109}Pt$, $^{111}Ag$, $^{111}In$, $^{113m}In$, $^{119}Sb$, $^{121m}Te$, $^{122m}Te$, $^{125}I$, $^{125m}Te$, $^{126}I$, $^{131}I$, $^{133}I$, $^{142}Pr$, $^{143}Pr$, $^{149}Pm$, $^{152}Dy$, $^{153}Sm$, $^{161}Ho$, $^{161}Tb$, $^{165}Tm$, $^{166}Dy$, $^{166}Ho$, $^{167}Tm$, $^{168}Tm$, $^{169}Er$, $^{169}Yb$, $^{177}Lu$, $^{186}Re$, $^{188}Re$, $^{189m}Os$, $^{189}Re$, $^{192}Ir$, $^{194}Ir$, $^{197}Pt$, $^{198}Au$, $^{199}Au$, $^{199}Au$, $^{201}Tl$, $^{203}Hg$, $^{211}At$, $^{211}Bi$, $^{211}Pb$, $^{212}Bi$, $^{212}Pb$, $^{213}Bi$, $^{215}Po$, $^{217}At$, $^{219}Rn$, $^{221}Fr$, $^{223}Ra$, $^{224}Ac$, $^{225}Ac$, $^{255}Fm$ and $^{227}Th$.

12. The method of claim 5, wherein the toxin is selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

13. The method of claim 5, wherein the immunomodulator is selected from the group consisting of a cytokine, a stem cell growth factor, a lymphotoxin, a hematopoietic factor, a colony stimulating factor (CSF), an interferon (IFN), an interleukin, erythropoietin and thrombopoietin.

14. The method of claim 13, wherein the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factors, interferon-α, interferon-β, interferon-γ, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and lymphotoxin.

15. The method of claim 1, wherein the anti-Trop-2 antibody or fragment thereof binds to the same epitope as an anti-Trop-2 antibody comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6).

* * * * *